(12) United States Patent
Cline et al.

(10) Patent No.: US 6,462,770 B1
(45) Date of Patent: Oct. 8, 2002

(54) IMAGING SYSTEM WITH AUTOMATIC GAIN CONTROL FOR REFLECTANCE AND FLUORESCENCE ENDOSCOPY

(75) Inventors: Richard W. Cline, Vancouver; John J. P. Fengler, North Vancouver; Curtis B. Figley, Edmonton; Remy Dawson; Bruno W. Jaggi, both of Vancouver, all of (CA)

(73) Assignee: Xillix Technologies Corp., Richmond (CA)

( * ) Notice: Subject to any disclaimer, the term of this patent is extended or adjusted under 35 U.S.C. 154(b) by 0 days.

(21) Appl. No.: 09/064,667

(22) Filed: Apr. 20, 1998

(51) Int. Cl.[7] ............................... A62B 1/04; A04N 9/47

(52) U.S. Cl. ........................................................ 348/65

(58) Field of Search ............................... 348/29, 65, 66, 348/70, 76, 68, 74, 71; 600/101, 109, 117, 118, 160, 166; 128/897, 6; H04N 9/47; H62B 1/04

(56) References Cited

U.S. PATENT DOCUMENTS

| | | | |
|---|---|---|---|
| 1,290,744 A | 1/1919 | Hollander |
| 2,453,336 A | 11/1948 | Orser |
| 2,857,523 A | 10/1958 | Corso |
| 3,582,178 A | 6/1971 | Boughton et al. |
| 3,671,098 A | 6/1972 | Rotter |
| 3,749,494 A | 7/1973 | Hodges |
| 3,790,248 A | 2/1974 | Kellow |
| 3,931,593 A | 1/1976 | Marshall |
| 3,970,373 A | 7/1976 | Pledger |
| 3,971,068 A | 7/1976 | Gerhardt et al. |
| 4,149,190 A | 4/1979 | Wessler et al. |

(List continued on next page.)

FOREIGN PATENT DOCUMENTS

| | | |
|---|---|---|
| EP | 0 774 865 A2 | 5/1997 |
| FR | 2 671 405 | 7/1992 |
| WO | WO 95/26673 | 10/1995 |

Primary Examiner—Chris Kelley
Assistant Examiner—Tung Vo
(74) Attorney, Agent, or Firm—Christensen O'Connor Johnson Kindness PLLC

(57) ABSTRACT

An imaging system for white light and fluorescence endoscopy that includes an automatic gain control circuit 30 that adjusts the brightness of an image produced based on distribution of pixel intensities in one or more video frames. The magnitude of the image signals produced by a pair of high sensitivity imaging devices such as intensified CCD transducers are compared to a number of reference thresholds. A time-over-threshold counter (112) determines the number of pixels in the image signals having magnitudes greater than or less than the reference thresholds. The distribution of pixel intensities is supplied to a decision tree algorithm (116) that determines whether the gain of the-intensified CCD transducers (44a, 44b) used to produced the autofluorescence images or the intensity of the excitation light produced by a light source (36) should be increased or decreased. In addition, a mode switch mechanism is provided to change rapidly from the fluorescence imaging mode to the white light imaging mode or vice versa. This mechanism includes provisions to prevent the accidental application of reflected white illumination light to the image-intensified CCD transducers. Proximity switches (192, 194) monitor the position of a light directing mechanism such as a mirror (186) to allow light to pass to fluorescence camera head (42) or to a color video camera head (46). The light source is not switched to produce white light until it is known that the mirror is in position to direct the reflected light to the color video camera head. Finally, the present invention produces a quantitative display of the relative intensities of the autofluorescence light produced in a pair of spectral bands.

18 Claims, 7 Drawing Sheets

U.S. PATENT DOCUMENTS

| | | |
|---|---|---|
| 4,155,812 A | 5/1979 | Akatsu |
| 4,158,504 A | 6/1979 | de Ponteves et al. |
| 4,200,801 A | 4/1980 | Schuresko |
| 4,260,217 A | 4/1981 | Traeger et al. |
| 4,378,571 A | 3/1983 | Handy |
| 4,556,057 A | 12/1985 | Hiruma et al. |
| 4,575,632 A | 3/1986 | Lange |
| 4,638,365 A | 1/1987 | Kato |
| 4,688,905 A | 8/1987 | Okamura |
| 4,786,813 A | 11/1988 | Svanberg et al. |
| 4,806,005 A | 2/1989 | Schneider et al. |
| 4,837,625 A | 6/1989 | Douziech et al. |
| 4,930,516 A | 6/1990 | Alfano et al. |
| 4,930,883 A | 6/1990 | Salzman |
| 4,951,135 A | 8/1990 | Sasagawa et al. |
| 4,954,897 A | 9/1990 | Ejima et al. |
| 5,007,408 A * | 4/1991 | Ieoka ............................ 128/6 |
| 5,028,128 A | 7/1991 | Onuki |
| 5,034,888 A * | 7/1991 | Uehara et al. ......... 364/413.13 |
| 5,041,852 A | 8/1991 | Misawa et al. |
| 5,115,308 A | 5/1992 | Onuki |
| 5,121,220 A | 6/1992 | Nakamoto |
| 5,128,803 A | 7/1992 | Sprafke |
| 5,132,837 A | 7/1992 | Kitajima |
| 5,214,503 A | 5/1993 | Chiu et al. |
| 5,282,082 A | 1/1994 | Espie et al. |
| 5,295,017 A | 3/1994 | Brown |
| RE34,622 E | 5/1994 | Ledley |
| 5,365,057 A | 11/1994 | Morley et al. |
| 5,371,355 A | 12/1994 | Wodecki |
| 5,377,686 A | 1/1995 | O'Rourke et al. |
| 5,408,263 A * | 4/1995 | Kikuchi et al. ................ 348/68 |
| 5,410,363 A | 4/1995 | Capen et al. |
| 5,419,323 A | 5/1995 | Kittrell et al. |
| 5,421,337 A | 6/1995 | Richards-Kortum et al. |
| 5,424,841 A | 6/1995 | Van Gelder et al. |
| 5,426,530 A | 6/1995 | Copenhaver et al. |
| 5,481,401 A | 1/1996 | Kita et al. |
| 5,485,203 A * | 1/1996 | Nakamura et al. .......... 348/263 |
| 5,507,287 A | 4/1996 | Palcic et al. |
| 5,535,052 A | 7/1996 | Jörgens |
| 5,557,451 A | 9/1996 | Copenhaver et al. |
| 5,585,846 A | 12/1996 | Kim |
| 5,590,660 A | 1/1997 | MacAulay et al. |
| 5,596,654 A | 1/1997 | Tanaka |
| 5,646,680 A * | 7/1997 | Yajima ........................ 348/74 |
| 5,647,368 A | 7/1997 | Zeng et al. |
| 5,677,724 A | 10/1997 | Takizawa et al. |
| 5,682,567 A | 10/1997 | Spruck et al. |
| 5,689,354 A | 11/1997 | Orino |
| 5,729,382 A | 3/1998 | Morita et al. |
| 5,749,830 A * | 5/1998 | Kancko et al. ............. 600/160 |
| 5,772,580 A | 6/1998 | Utsui et al. |
| 5,838,001 A | 11/1998 | Minakuchi et al. |
| 6,059,720 A * | 5/2000 | Furusawa et al. ........... 600/160 |
| 6,120,435 A * | 9/2000 | Eino ......................... 600/118 |
| 6,148,227 A | 11/2000 | Wagnières et al. |

\* cited by examiner

IMAGING SYSTEM WITH AUTOMATIC GAIN CONTROL FOR REFLECTANCE AND FLUORESCENCE ENDOSCOPY

FIELD OF THE INVENTION

The present invention relates to imaging systems for medical endoscopy, in general and to endoscopic imaging systems for fluorescence and reflectance endoscopy, in particular.

BACKGROUND OF THE INVENTION

One common diagnostic technique used by physicians to detect diseases within a body cavity of a patient is white light optical fiber endoscopy. With this technique, white light is directed into the body cavity via a non-coherent fiber-optic illumination guide of an endoscope. The light illuminates the tissue under examination and the reflected illumination light is gathered and transmitted through a coherent fiber-optic imaging guide of the endoscope. The image formed by the reflected white light at the end of the imaging guide may be viewed directly through the endoscope eyepiece or may be imaged by a color video camera connected to the eyepiece. Images transduced by the camera are then typically transmitted to an image processing/storage device and to a video monitor where they can be viewed by the physician.

To aid physicians performing endoscopy in detecting the presence of cancerous or pre-cancerous tissue, the differences in the autofluorescence (also referred to as native fluorescence) spectrum of normal and abnormal tissue can be exploited. In fluorescence optical fiber endoscopy, a fluorescence excitation light is delivered into the body cavity via the illumination guide of the endoscope. The wavelengths of this light are matched to the absorption spectrum of the naturally occurring fluorescing molecules (or fluorophores) present in the tissue (i.e., to blue light). The fluorescence excitation light causes the tissue in the body cavity to fluoresce with a green and red emission spectrum and the resulting light is collected and transmitted through the optical fiber imaging guide of the endoscope. The resulting image is transduced by a camera that filters out any reflected blue light and divides the autofluorescence into two broad (green and red) spectral bands. The image formed by the light in each spectral band is projected onto a separate intensified CCD (ICCD) transducer and the resulting signal is fed into a control center for processing, storage and, finally, for display on a video monitor. The difference in the autofluorescence emission spectrum of normal and abnormal tissue is presented as a difference in color on the video monitor.

Systems for fluorescence fiber endoscopy are fully described in U.S. Pat. Nos. 5,507,287; 5,590,660, 5,647,368 and 4,786,813 that are assigned to Xillix Technologies Corp. of Richmond, BC, Canada, the assignee of the present invention, and are sold by Xllix as the Xillix® LIFE-Lung Fluorescence Endoscopy System® (the "LIFE-Lung System"). Multi-center clinical trials have shown that by using the Xllix LFE-Lung System as an adjunct to white light endoscopy, the physician's sensitivity in detecting moderate dysplasia, or worse, is 2.71 times greater than the sensitivity of a physician using white light endoscopy alone.

The current LIFE-Lung System has a number of limitations, however. First, the current embodiment of the system requires the physician to manually adjust the gain of the system (i.e., to increase and decrease the camera's sensitivity to the tissue autofluorescence). This is a cumbersome task for the physician to perform, when he/she is simultaneously trying to maneuver the endoscope in the patient. Although automatic gain control circuits for video systems are widely available, they do not provide adequate gain control for the complex scene conditions encountered in imaging autofluorescence with ICCDs. If, for example, the average brightness of an image is increased to an acceptable level, there may be bright spots that can damage the ICCDs. Similarly, if the peak brightness of an image is reduced to prevent localized image saturation, the remainder of the image may become too dark to be recognizable. Furthermore, commonly available average and peak-based automatic gain control circuits do not provide images with a good dynamic range under a variety of viewing conditions, i.e. with an optimized contrast. In endoscopy, these viewing conditions include situations whereby the range of fluorescence light intensities are greater than the dynamic range of ICCDs and the image scenes vary from complex structures (i.e. lots of intensity variations) to flat structures (i.e. homogeneous).

A further complication with the use of an automatic gain control circuit arises due to the fact that the gain relationship between the two channels (green and red) of the imaging system must follow a defined function. If the gain of each channel is varied independently, the colors in the resulting video image will not consistently reflect the spectral differences in the autofluorescence of the tissue.

A second limitation of the current LIFE-Lung System becomes evident when a physician wishes to switch between white light (reflectance) and fluorescence imaging modes. With the current system, the physician must switch light sources and cameras manually (i.e., from a white light illumination source to a fluorescence excitation light source and from an RGB color video camera to the fluorescence camera). One technique for addressing this time consuming process is to have all light sources and cameras connected to the endoscope simultaneously and to utilize a mode switching mechanism to switch from one imaging mode to the other. However, some precaution must be taken in the implementation of a switching mechanism since the ICCDs can be damaged if they are subjected to the bright, reflected illumination light. Care must be taken to ensure that the ICCDs are not energized unless the appropriate illumination conditions exist.

A third limitation of the current LIFE-Lung System is that a physician viewing the image displayed by the system has no way of objectively quantifying the extent of abnormality exhibited by the tissue under examination. The effective use of the system is dependent on such subjective factors as the physician's ability to distinguish color and his/her ability to interpret this color information in the context of other image features. A means to objectively quantify the difference in the autofluorescence spectra of normal and abnormal tissue, or even an additional means to subjectively differentiate these tissues based on their difference in autofluorescence spectra could improve the clinical usability of this system. This can be accomplished using computational techniques using the spectral information of the emitted fluorescence and displaying the results on the monitor together with the images.

In summary, the operation of current fluorescence endoscopy systems may be significantly improved by:
  a) an automatic gain control circuit that will optimally adjust the brightness of autofluorescence images and that will maintain a defined relationship between the two channels of the imaging system;

b) a mechanism that allows rapid switching between white light and fluorescence imaging modes, while preventing the accidental exposure of energized ICCDs to damaging light intensities; and c) a means of utilizing the differences in the autofluorescence emission spectra of normal to abnormal tissue to objectively quantify the degree of abnormality of the tissue.

SUMMARY OF THE INVENTION

The present invention is an imaging system for white light and fluorescence endoscopy that includes a particular automatic gain control (AGC) circuit in the fluorescence imaging mode. The AGC circuit adjusts the gain of the imaging system by adjusting the gain of two high sensitivity imaging devices such as image intensified CCD (ICCDs) transducers in a fluorescence camera head and by adjusting the light intensity of the excitation light source. The video signals from a pair channels (the "green" and "red" channel) of a fluorescence camera are supplied to a set of counters. The counters, consisting of counters connected to a clocking oscillator, measure the length of time each video signal has a magnitude that exceeds a reference threshold that is individually set for each counter. Thus, by appropriately arranging the threshold levels, the outputs of the counters can be made to indicate the distribution of video signal amplitudes in one or more video fields. Based upon the outputs of the counters, a decision tree algorithm determines if the gain of the imaging system or the light source intensity should be increased or decreased. A gain control equation determines the appropriate value of light source intensity change and maps the resulting imaging system gain increase or decrease to an individual gain change for each ICCD transducer such that the relative gain between the two channels remains the same.

The present invention also includes a mode switching mechanism that allows for convenient switching between white light and fluorescence endoscopy imaging modes. The implementation of mode switching implies that white light and fluorescence light sources and cameras are connected to the endoscope simultaneously and that the appropriate combination of camera and light source are activated when switching modes. This requires a two-part mode switching mechanism: one switching the cameras and one switching the light sources. The camera mode switching mechanism consists of a light directing mechanism such as a mirror that is movable between a first position, where the image from the endoscope is reflected towards an RGB video camera head, and a second position, where the image from the endoscope is allowed to pass to the fluorescence camera head. When a physician uses the mode switch to change from white light imaging to fluorescence imaging or vice versa, a pair of proximity switches provide signals to the system control center, which monitors the position of the mirror, to ensure that the ICCDs are not energized until the appropriate light source has been selected. The light source mode switching mechanism consists of a filter driver that positions blue, fluorescence excitation filters or white light filters in an illumination light path that extends between the light source and an endoscope.

The present invention also provides a means of objectively quantifying the spectral differences between normal and abnormal tissue by using the relative brightness of autofluorescence in the spectral bands being imaged (green and red). A portion of the autofluorescence image is analyzed and the numerical value defined by a particular mathematical function such as the ratio of the image brightnesses of the two wavebands is displayed for the physician.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is an imaging system for white light and fluorescence endoscopy that includes an automatic gain control (AGC) circuit in the fluorescence imaging mode. The AGC circuit controls the image brightness in two ways, a) by adjusting the gain of the two image-intensified CCDs (ICCDs) transducers in a fluorescence camera head, and b) by adjusting the intensity of an excitation light source. The input to the AGC circuit are the two video signals (a green and red channel) produced by the fluorescence camera. The video signals are supplied to a set of counters that determine a total period of time during which the video signal has a magnitude that exceeds reference threshold (set individually for each counter). The outputs of the counters are indicative of the distribution of video signal amplitudes in one or more video fields. Based upon the outputs of the counters, a decision tree algorithm determines if the gain of the imaging system or light source intensity should be increased or decreased. A gain control equation determines the appropriate value of light source intensity change and maps the gain increase or decrease to an individual gain change for each ICCD such that the relative gain between the two channels remains the same.

Figure 1:
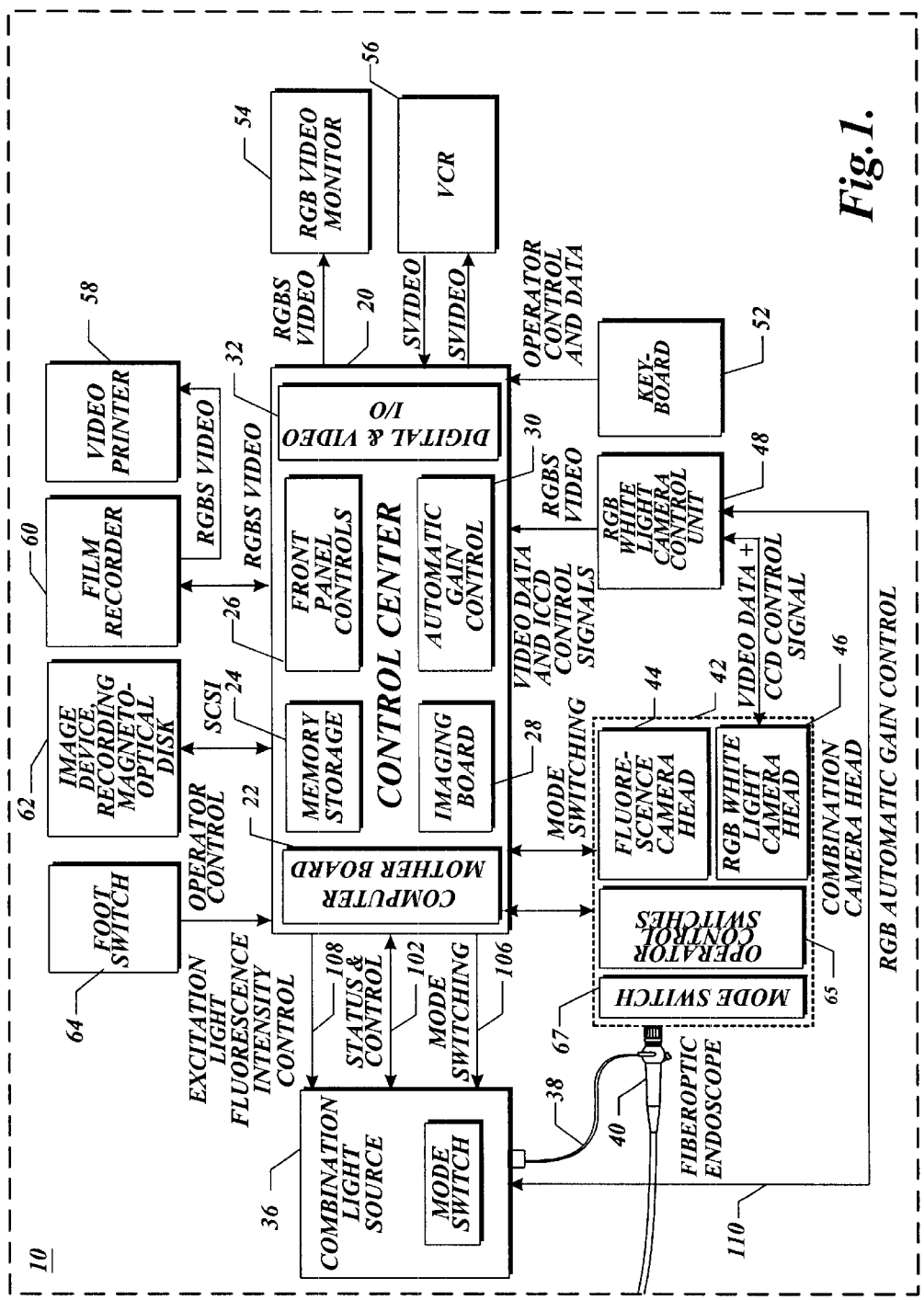
FIG. 1 is a block diagram of an imaging system for white light and fluorescence endoscopy according to the present invention.

FIG. 1 is a block diagram of an imaging system 10 for white light and fluorescence endoscopy according to the present invention. At the heart of the imaging system is a control center 20 that includes a central processing unit 22 that is programmed to control the operation of the system including a combination light source 36 and a combination camera head 42. An internal random access memory (RAM), a hard disk drive and read-only memory (ROM) 24 stores a computer software program that controls the operation of the central processing unit 22. The memory also allows the storage of data such as acquired images, parameters and log files. A number of controls 26 on a front panel of the control center 20, allow an operator to adjust the operation of the imaging system.

The control center 20 also includes an imaging board 28 that receives analog video signals that originate from a number of sources including a fluorescence camera head 44 and an RGB camera head 46 that are enclosed within the combination camera head 42. A video switch, that is part of a digital and video I/O 32, receives and selects the fluorescence or RGB video signals to be supplied as an input to the imaging board. The imaging board 28 digitizes the selected video signal, then processes and converts the digitized signals to appropriate signals to be displayed on a video monitor 54.

An automatic gain control circuit 30, included within the control center 20, automatically adjusts the gain of the autofluorescence camera head 44 and the intensity of the fluorescence excitation light from the combination light source 36.

The combination light source 36 provides the white light and fluorescence excitation light. The control center 20 is interfaced with the light source 36 through status and control lines 102, 106, and 108. Broadband white illumination light or fluorescence excitation light (typically at 437 nm±10 nm) is supplied from the combination light source 36 to an illumination guide 38 of a fiber-optic endoscope 40. Light from the illumination guide 38 illuminates an internal body cavity of a patient. Reflected white light or autofluorescence light from the tissue under examination is transmitted by an imaging guide of the fiber-optic endoscope 40 and is projected onto the combination camera head 42. The combination camera head 42 also includes a mode switch mechanism 67 that directs the light received from the endoscope 40 to either the RGB video camera head 46 or the fluorescence camera head 44. With the fluorescence imaging mode selected, the fluorescence camera head 44 produces electronic signals that are routed to a dual channel fluorescence camera control unit within the control center 20 (not shown) that converts the electronic signals to standard video signals. The video signals are then routed through the video I/O 32 to the imaging board 28 where they are processed before being displayed on the RGB video monitor 54. Alternatively, if the physician desires to view a reflectance white light image, the position of the mode switch mechanism 67 is selected to project the reflected illumination light onto an RGB video camera head 46. The electronic signals produced by the camera head 46 are supplied to an RGB camera control unit 48 that is external to the control center 20, where they are converted to RGB video signals. The white light RGB video signals are also routed through the video I/O 32 to the imaging board 28 and are processed before being displayed on the RGB video monitor 54. The RGB video camera control unit 48 includes an automatic gain control circuit that also has the capability of adjusting the intensity of the light produced by the combination light source 36 when the system is operating in white light mode. The automatic gain control signals for the white light mode are transmitted to the combination light source on a lead 110.

A keyboard 52 interfaces with the control center 20 through the digital I/O 32 on the computer motherboard and allows the operator to enter patient data or to change the operating parameters of the imaging system.

In order to display the white light and fluorescence images, the RGB video monitor 54 is connected to the control center 20 through the video I/O 32. A VCR 56 may be connected so that video images can be recorded for later review and analysis. A video printer 58 allows a physician to print hard copies of a video frame. Images may also be recorded by a film recorder 60 or stored on a magneto-optical disk 62.

To allow a user to control the operation of the imaging system, several programmable operator input devices are provided. A footswitch 64 and three operator control switches 65 on the camera head 42 allow the operator to remotely activate various control center 20 functions such as freezing and storing images, selecting different AGC modes, or to control some of the peripheral devices such as the video printer 58, film recorder 60, or magneto optical disk 62.

Figure 2:
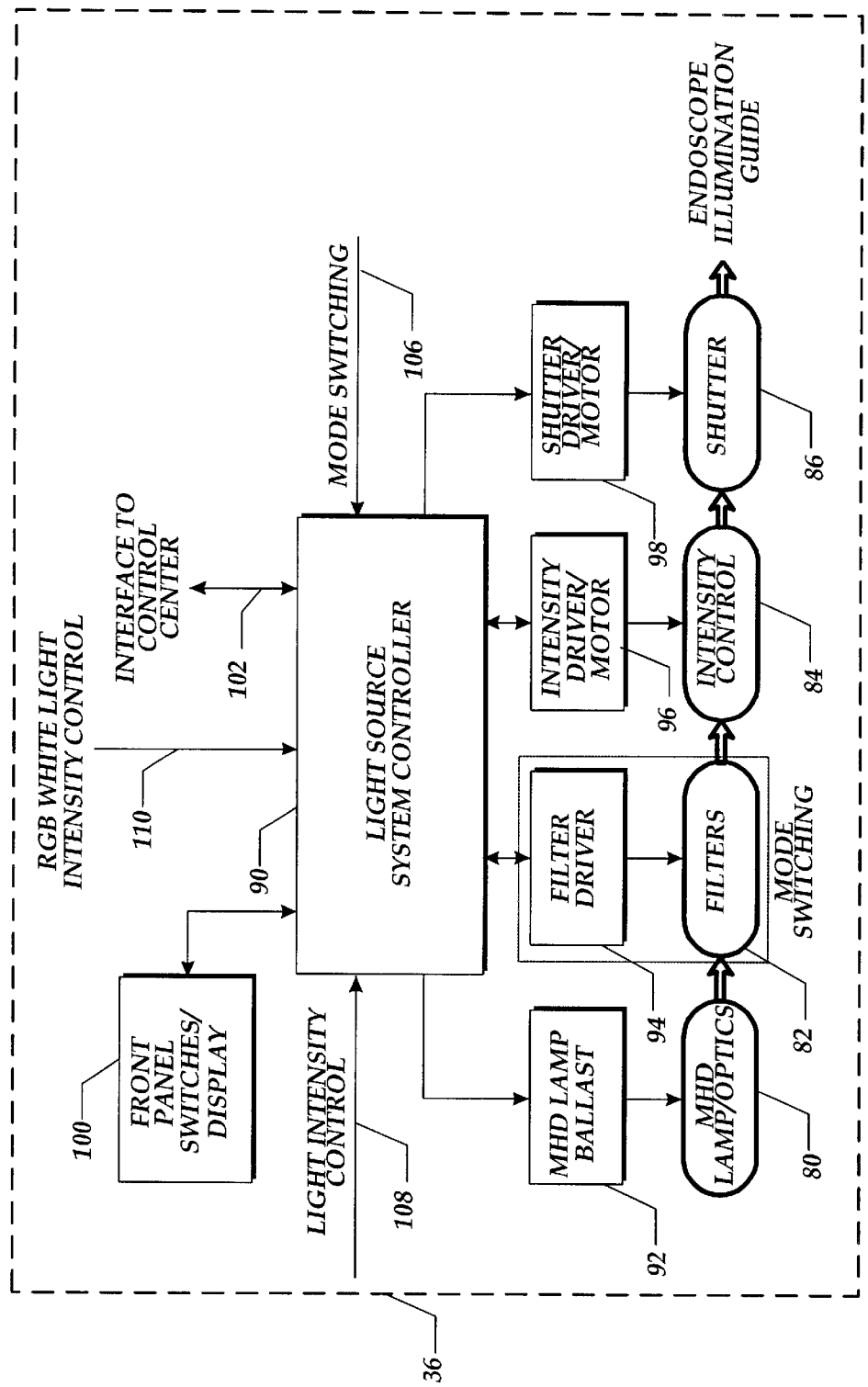
FIG. 2 is a block diagram of a light source used in the imaging system for white light and fluorescence endoscopy shown in FIG. 1.

FIG. 2 illustrates in further detail the combination light source 36 that is shown in FIG. 1. The light source includes a metal halide lamp 80 that produces broadband white light with mercury (Hg) peaks. Light produced by the lamp 80 is passed through a number of filters 82. Depending on the imaging mode selected, the light is transmitted through either a broadband white light filter (i.e. triple notch filter to remove the Hg peaks) that eliminates the Hg peaks and shapes the spectrum of the metal halide lamp so that it is similar to that of a Xenon lamp. Alternatively, if fluorescence imaging is selected, light from the lamp is passed through a blue fluorescence excitation light filter that comprises a blue pass band having a center frequency near the mercury peak that occurs at 437 nanometers.

Light passing through the filters 82, also passes through an adjustable intensity control mechanism 84, which controls the intensity of the light delivered to an endoscope. The intensity control 84 is preferably a metal plate with an appropriate shape to block a variable amount of light when it is moved in and out of the light path.

After passing through the intensity control mechanism 84, the light passes through a shutter mechanism 86 that opens to allow the light to enter the illumination guide of the endoscope, if the latter is plugged in.

The operation of the combination light source 36 is controlled by a microprocessor-based light source controller 90. The light source controller 90 controls the operation of a metal halide lamp ballast 92 that provides the operating voltage for the metal halide lamp 80. In addition, the light source controller provides control signals to a filter driver 94, that physically moves one of the filters 82 into the light path in accordance with time imaging mode selected.

An intensity control driver 96 receives control signals from the light source controller 90 in order to move the intensity control 84 in and out of the light path, and thereby varies the intensity of the light that reaches the illumination guide of the endoscope. The light source controller 90 also sends control signals to a shutter driver/motor 98 that causes the shutter mechanism 86 to open and close.

In addition to controlling the components that adjust the intensity and wavelength of light that is provided to the illumination guide of the endoscope, the light source controller 90 also interfaces with a number of front panel switches 100 that allow a physician to manually adjust the operation of the light source. Alternatively, the light source controller 90 receives commands to control the light source from an interface to the status and control lines 102 that is coupled to the control center 20 that controls the overall operation of the imaging system as shown in FIG. 1.

To change the output of the combination light source 36 from white illumination light to blue excitation light or vice versa, as well as to control the intensity of the light produced, the light source controller 90 also receives control signals from the control center on lead 106 that indicate which of the filters 82 should be placed into the light path in order to create the white light illumination or blue excitation light. The light source controller 90 receives signals from the control center on the status and control lines 108 that indicate whether the intensity of the excitation light produced should be increased or decreased. Finally, the light source controller 90 receives signals from the RGB video camera control unit 48 on the lead 110 that adjusts the intensity of the white illumination light produced.

Figure 3:
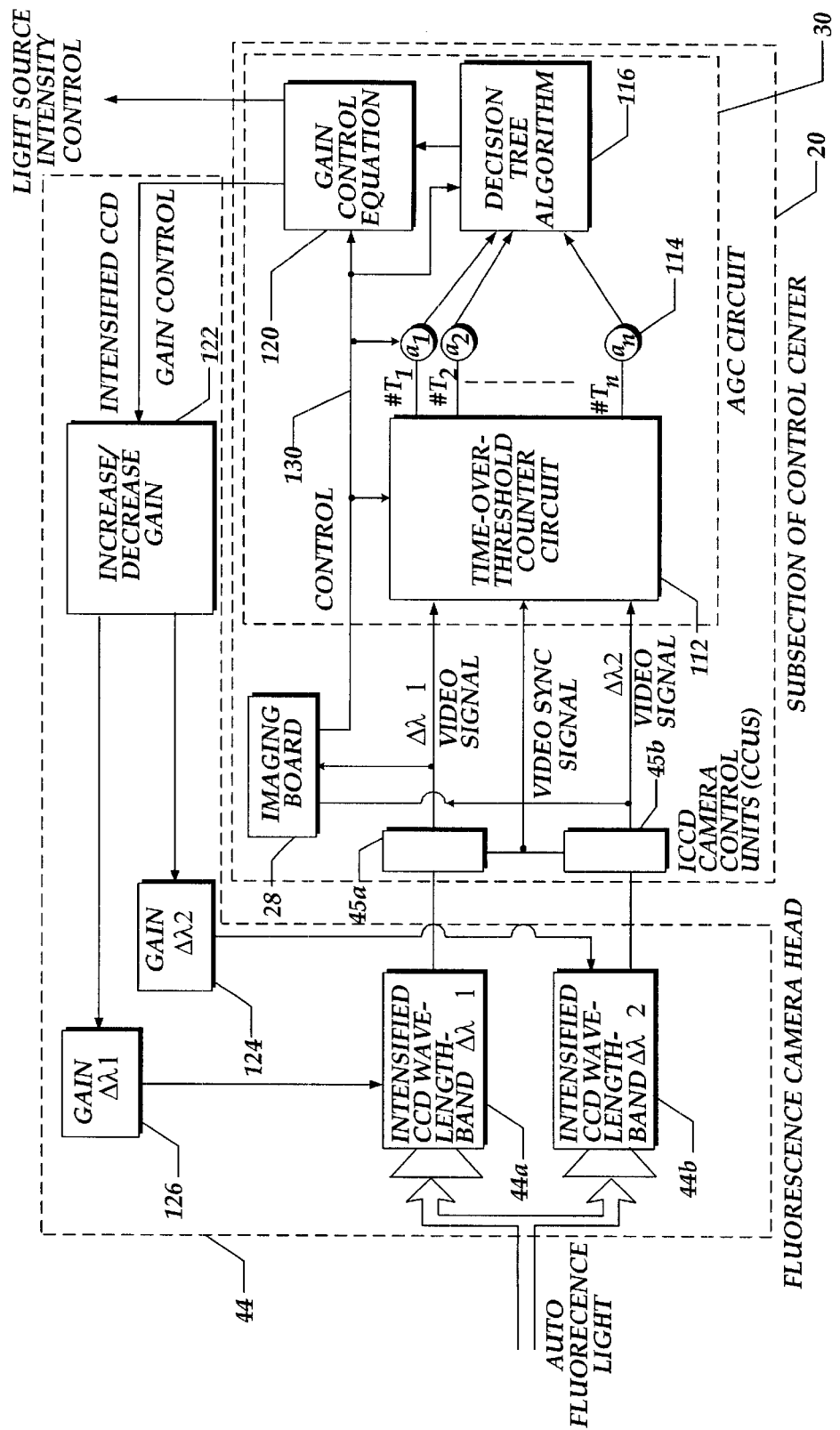
FIG. 3 is a block diagram of an automatic gain control circuit in accordance with a first aspect of the present invention.

To eliminate the need for a physician to manually adjust the gain while in the fluorescence imaging mode, the imaging system of the present invention includes a fluorescence mode automatic gain control (AGC) circuit 30 as shown in FIG. 3. The imaging system can also be operated under manual control as the current Xillix LIFE-Lung Fluorescence Endoscopy System®. The implementation of the fluorescence mode AGC is as follows: As described previously, autofluorescence light produced by the tissue under examination is divided into a pair of spectral bands and projected onto a pair of high sensitivity imaging devices such as a pair of electron bombarded CCD's or image intensified CCD transducers 44a and 44b. The transducer 44a receives the light in a wavelength band $\Delta\lambda_1$, which is located in the green portion of the visible spectrum, while the transducer 44b receives light in a wavelength band $\Delta\lambda_2$, which is located in the red portion of the visible spectrum. The electronic signals produced by the intensified CCD transducers 44a and 44b are supplied to camera control units (CCUs) 45a and 45b within the control center 20, where they are converted into video signals and routed through the video I/O 32 to the imaging board 28 and to the AGC circuit.

The video signals routed to the AGC circuit are applied to a time-over-threshold counter circuit 112. The counter circuit also receives a clock signal which is gated by the horizontal and vertical sync signals from the CCUs. The counter 112 produces a number of outputs #T1, #T2, . . . #Tn, each of which contains a value which is proportional to the area in one or more video fields that has an intensity level above an associated predefined threshold intensity value. Each of the output values #T1, . . . #Tn, may be weighted by a function $a_1, \ldots a_n$ 114 before being supplied to a decision tree algorithm 116. The decision tree algorithm 116 determines if the gain of the imaging system and/or the intensity of the light produced by the combination light source 36 should be increased or decreased. The output of the decision tree algorithm 116 indicates the amount by which the gain should be increased/decreased and this signal is supplied to a gain control equation 120. The gain control calculates the amount by which the light source intensity and/or the gain of the individual intensified CCD transducers 44a and 44b of the imaging system should be adjusted to meet the gain change determined by the decision tree algorithm, while maintaining a predefined gain relationship between the two channels.

If the camera gain is to be increased or decreased, the gain control equation 120 produces a pair of binary numbers whose magnitude will result in a proportional gain change in the two ICCDs. An increase/decrease gain control circuit 122 receives the binary numbers from the gain control equation 120 and converts the binary numbers received into a pair of voltage levels that are supplied to a pair of transducer gain controls 124 and 126. The transducer gain controls 124 and 126 adjust the absolute gain of the intensified CCD transducers 44a and 44b respectively.

Figure 4:
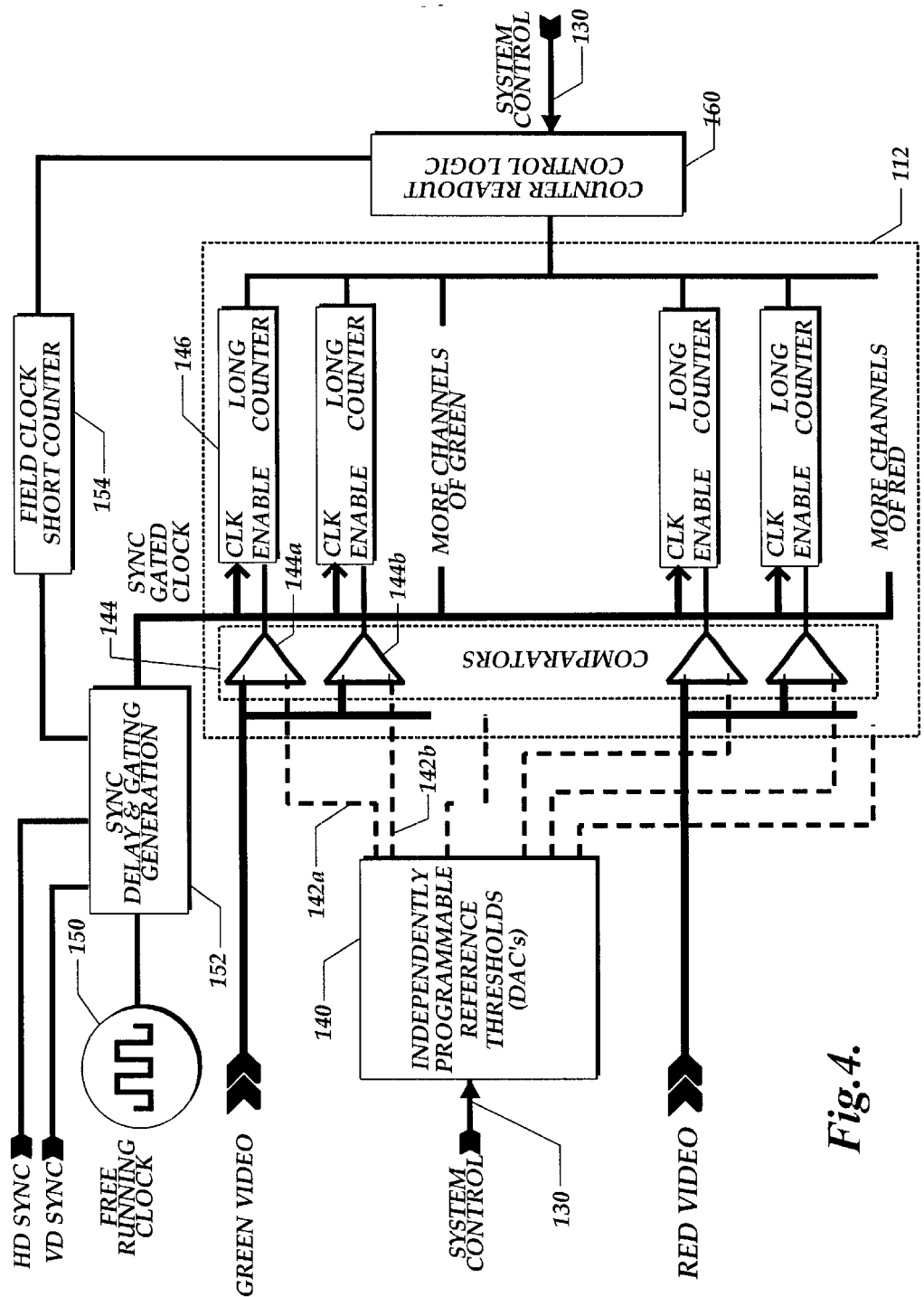
FIG. 4 is a block diagram of a number of comparators and time-over threshold counters that are included in the automatic gain control circuit shown in FIG. 3.

FIG. 4 illustrates in greater detail the time-over-threshold counter 112 described above. The counter 112 operates to produce numeric counts that are indicative of how long a threshold intensity is exceeded in one or more video frames. These numeric counts are proportional to the area in an image with an intensity above a predefined value. A bank of independently programmable, reference threshold digital-to-analog converters 140 is programmed by the control center 20 to set a series of reference threshold levels against which the video signals from the CCUs are compared. The particular reference threshold levels are selected to represent a percentage of the zero to full scale video signal that is produced by the CCUs and their chosen values are generally dependent on the type of tissue being examined, as will be described below.

The reference thresholds are applied to the inverting inputs of a number of comparators 144. For example, a voltage equal to 45% of the full scale range of the green channel video signal is supplied on a lead 142a to an inverting input of a comparator 144a. Similarly, a voltage equal to 75% of the full scale range is supplied on a lead 142b to an inverting input of a comparator 144b. Another set of reference threshold voltages are applied to a set of comparators that receive the video signal produced by the red channel CCU. In the presently preferred embodiment of the invention, one reference threshold for each channel is set at a desired peak value while the other reference threshold is set at a desired average intensity value.

The video signals produced by the dual channel fluorescence CCUs are applied to the noninverting inputs of the comparator circuits 144. When the voltage level of the video signals exceeds the reference thresholds set by the digital-to-analog converters 140, the comparators 144 produce logic high signals. Associated with each of the comparators 144 is a 24-bit counter 146. Each counter has a counter enable pin coupled to the output of its associated comparator such that when the comparator produces the logic high signal, the counter is enabled.

As indicated above, the automatic gain control circuit 30 includes a free running clock 150 having a frequency that is substantially equal to the pixel clock of the CCUs. A sync delay and gating circuit 152 receives the horizontal and vertical synchronization signals produced by the CCUs and only passes the free running clock 150, during the active portions of the video signals. The sync delay and gating circuit 152 also produces a field clock pulse for each field of the video signals received. The pulses are counted by a short counter 154 in order to keep track of the number of field periods associated with the values contained in the time-over-threshold counters.

When the counters 146 are enabled by their corresponding comparator circuits 144, the counters 146 count the number of sync-gated clock pulses that occur during the time when the video signals produced by the red or green channel CCUs exceed the reference threshold associated with the comparator that is connected to the counter's enable pin.

The values in the counters 146 are read out through a counter readout control circuit 160 that connects the counters 146 to the imaging system's data bus 130 located on a motherboard within the control center 20. The counter readout control circuit also receives the count held in the short counter 154. The short counter 154 allows the software to be programmed to read out the counters 146 at periodic intervals, such as every ten fields, etc.

Although the presently preferred embodiment of the invention utilizes two reference thresholds for each of the green and red channels, additional threshold counters can be added to the automatic gain control circuit in the manner described above if it is desired to obtain more detailed information on the distribution of the video signal amplitudes.

Figure 5:
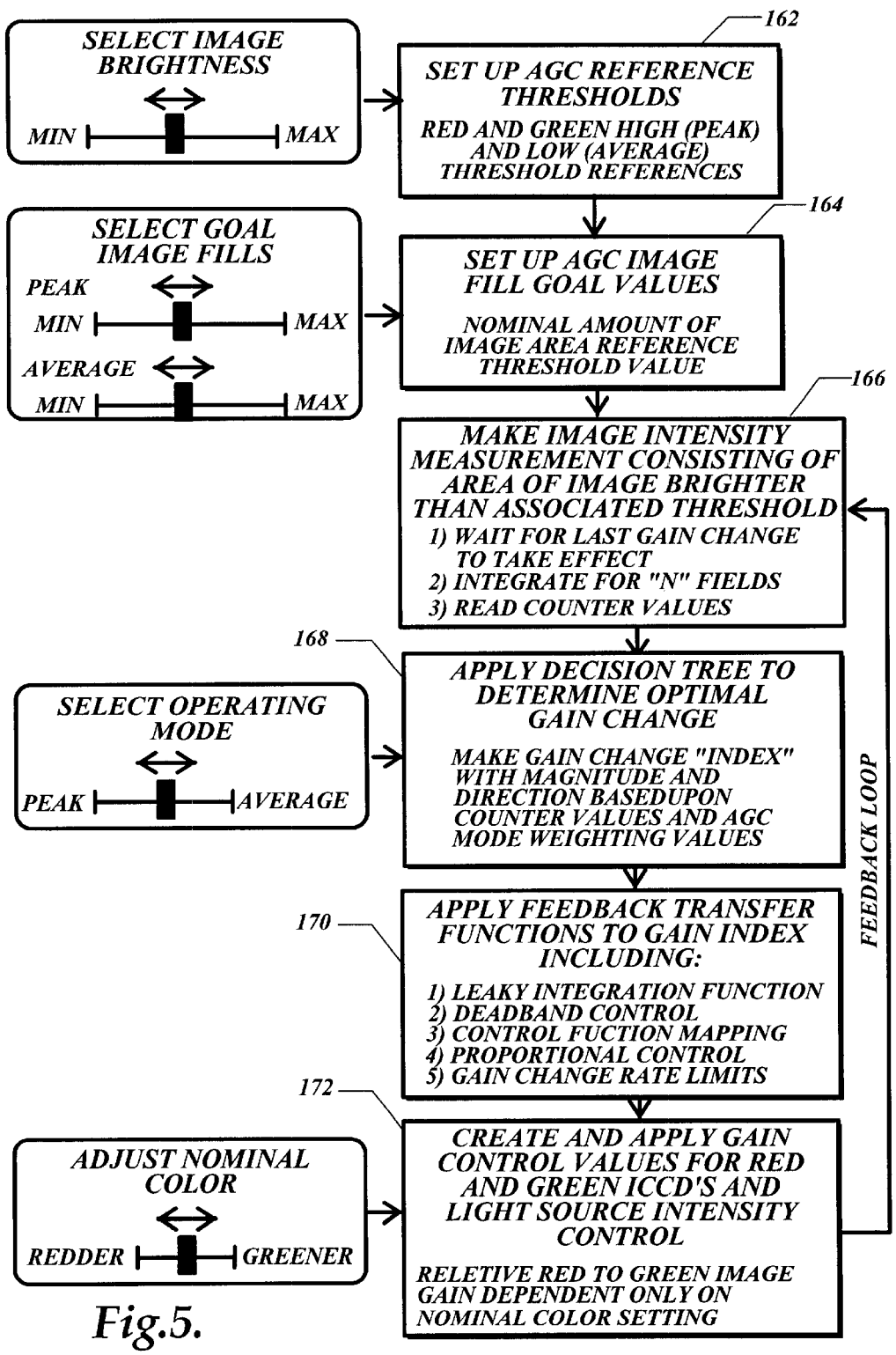
FIG. 5 is a flowchart illustrating the steps performed by the present invention to change the gain of the imaging system shown in FIG. 3 or the intensity of light produced by the light source shown in FIG. 2.

FIG. 5 illustrates the steps performed by the decision tree algorithm 116 and the gain control equation 120 shown in FIG. 3 to adjust the gain of the ICCDs and the light source intensity. FIG. 5 illustrates the two basic processes used to implement the automatic gain control, namely, i) the setup of the parameters in steps 162 and 164, and ii) the running of the decision tree algorithm and gain control equation in steps 166 to 172.

Beginning with a step 162, the peak and average reference thresholds are set. These values are selected by the operator using the system software. The values selected depend upon the type of image being viewed. In an image that contains many structural features, the thresholds are selected to ensure that all details remain visible. For example, when viewing a body cavity containing detailed structure such as the bronchi, the peak reference threshold may be set at 90% of the full scale value and the average reference threshold set at 50% of the full scale value. Alternatively, if the body cavity being examined is relatively homogeneous, such as the stomach, the reference threshold values may be set such that the average intensity of the image ensures a relatively bright image. For example, the peak reference threshold may be set at 80% of full scale and the average reference threshold set at 60% of full scale. Preprogrammed thresholds selected for commonly viewed tissue samples can be selected or custom values can be entered.

At a step 164, the automatic gain control circuit selects a number of AGC image fill goal values. These values represent the nominal image area for which the video signal amplitude must be greater than or equal to a particular threshold. For example, fill goal values may be chosen such that 2% of the image area has video signal amplitudes greater than the peak threshold value and 55% of the image area has video signal amplitudes greater than the average threshold value. The automatic gain control circuit adjusts the gain of the ICCDs and/or the intensity of the light source such that the image intensity distribution calculated from the time-over-threshold counter 112 achieves the best match to the desired image fill goal values. Like the threshold values, the fill goal values are selected by the operator of the system.

Step 166 is the first step in the actual AGC decision tree algorithm. At a step 166, the automatic gain control circuit waits for the last gain change to take effect and then measures the image intensity distribution for specified number fields. At the end of the specified number fields, the values from the counters 146 in the time-over-threshold counter circuit 112 are read and the image areas analyzed.

The image area having video signal amplitudes above the higher, or "peak" threshold, and the image area having video signal amplitudes above the lower, or "average" threshold, are applied to the decision tree at step 168. The decision tree determines whether the gain should be changed so that the intensity distribution will better meet the AGC fill goal values desired. As discussed above, the image area allowed to exceed the peak or the average threshold may be weighted by the functions 114, in order to make the automatic gain control circuit operate more like a peak or average value control circuit as desired for the particular viewing situation.

The amount of gain change determined by the decision tree algorithm 116 is modified by well known process control techniques at a step 170 to optimize transient behavior such as overshoot, settling time, and oscillatory behavior. These techniques include a leaky integrator function, dead-band control, control function mapping, proportional control, and rate and range limiting actions on the next applied gain change. These techniques ensure gain changes occur as quickly as possible without creating stability problems.

At a step 172, the gain change for the green or red channel ICCD is determined and if required, the amount of light source intensity change. The gain change is modified by the control techniques and is applied to the gain control equation 120. This equation relates the gain setting of the ICCD in each of the two channels, such that the ratio (first order polynomial) of the gains between the two channels is maintained. The ratio of the gains between the two channels may be selected by the system operator. The operator may adjust the ratio, such that the resulting video image appears more red or more green as desired. In the presently preferred embodiment of the invention, the relative gain of the ICCD in the red channel to the ICCD in the green channel can be varied over a range of 0.75 to 3. In some applications, the relationship between the gains of the two channels may be a higher order polynomial, e.g. $g_1 = c + ag_2 + bg_2^2 + \ldots$ where $g_1$ is the gain of the red channel, $g_2$ is the gain of the green channel and a, b, c, are constants.

The situation may occur that the required fluorescence camera gain falls outside of the optimal gain adjustment range of the ICCD in one or both of the channels. If the calculated gain setting of either channel is greater than the maximum optimal setting or smaller than the minimum optimal setting, then the intensity of the excitation light source is increased or decreased by a fixed amount. The intensity of the light produced by the light source is adjusted a sufficient amount to return the camera gain settings to within the optimal working range. A pseudocode listing of the decision tree algorithm 116 and gain control equation 120 is set forth in Appendix A.

Figure 6:
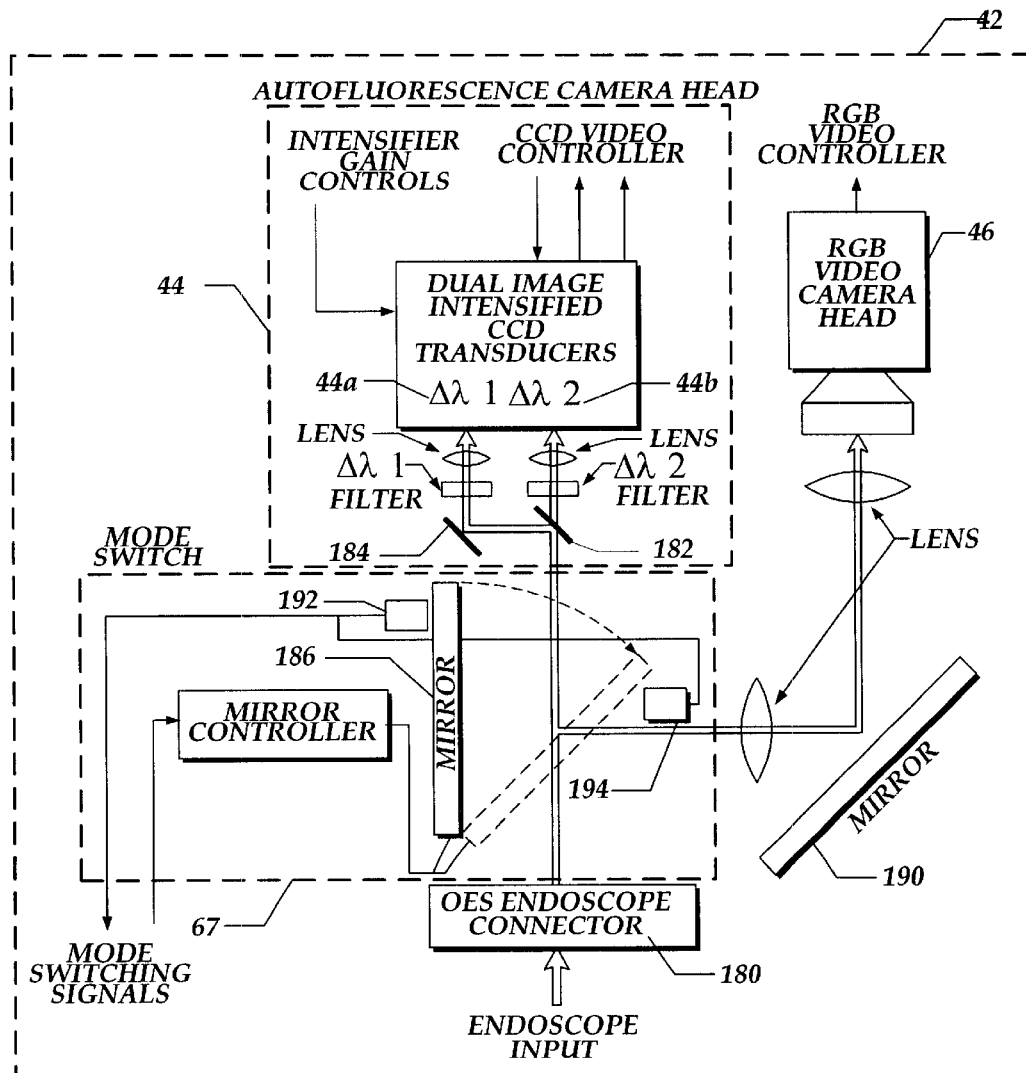
FIG. 6 is a block diagram of an imaging mode switching mechanism located in the combination camera head in accordance with another aspect of the present invention.

The present invention also includes a two part mode switch mechanism (one part in the light source and one part in the combination camera head) that allows for convenient switching between white light and fluorescence endoscopy imaging modes. FIG. 6 is a schematic block diagram of the mode switching mechanism of the combination camera head. The switching mode mechanism of the light source is shown in FIG. 2. The preferred embodiment of the mechanism requires the endoscope to be attached to the combination light source 36 and the combination camera head 42 by means of the endoscope connector 180. The combination light source 36 is capable of providing white light (reflectance) illumination and blue light (fluorescence excitation) illumination. The combination camera head 42 is capable of transducing three channel RGB reflectance images and two channel fluorescence images.

Because the light source 36 and camera head 42 are physically separate, the mode switching mechanism is composed of two parts. The two parts of the mechanism are linked through control signals via the imaging system control center 20 and the light source system controller 90. Since the metal halide lamp 80 in the combination light source 36 is capable of providing both the white and blue light, a light source part of the mode switch consists of the filter driver 94 and the white light an blue light filters 82. The filter driver 94 responds to instructions from the light source system controller 90 and positions the appropriate filter in the light path between the lamp and the endoscope illumination guide. The status of the filter driver 94 is also monitored by the light source system controller 90, which then communicates with the control center 20 via the interface to the status and control lines 102.

A second part of the mode switching mechanism is located in the combination camera head 42. This part of the mode switching mechanism 67 utilizes a movable light path directing mechanism such as a mirror 186. When in the imaging system is in fluorescence imaging mode, the mirror is moved out of the light path between the endoscope eyepiece and the fluorescence camera head 44. In this way the fluorescence light reaches the dichroic mirror 182 that separates spectrally $\Delta\lambda_1$ and $\Delta\lambda_2$ into their respective optical paths. When the imaging system is in the white light imaging mode, the mirror 186 is moved into the light path. In this position, light from the endoscope is directed to a second, fixed mirror 190, where the light path is folded to form a periscope that redirects the light from the endoscope eyepiece to the RGB video camera head 46.

The operation of both parts of the mode switching mechanism is controlled by an operator input on the combination camera head 42. The operator initiates a switch 65 to change the operation of the imaging system. This results in a signal being sent to the control center indicating that a switch of imaging modes has been initiated. A signal is generated by a pair of electrical or optical proximity switches 192, 194 in the combination camera head 42 that sense the position of the movable mirror 186. A second signal is generated by switches 192, 194 and sent to the control center 20 when the movable mirror 186 has reached its new position.

The switches 192, 194 function as a safety mechanism for the ICCDs in the fluorescence camera head. When energized, the ICCDs are susceptible to damage from bright light (e.g. white light reflectance images from the endoscope eyepiece). If the movable mirror 186 is not completely in the fluorescence mode imaging position, the control center 20 reacts by immediately shutting off the power to the ICCDs, thereby protecting them from exposure to possibly damaging illumination.

The control center 20 reacts differently to the switch signals depending on whether the operator is switching from fluorescence imaging mode into the white light imaging mode or from white light imaging mode into the fluorescence imaging mode. In the former case, the control center 20 reacts to the first switch signal by immediately shutting off the power to the ICCDs and stopping the display of all images. When the control center 20 receives the second switch signal, indicating that the movable mirror 186 in the camera head 42 has reached the white light imaging mode position, the control center sends a signal to the light source system controller 90 instructing it to move the white light filter into the light path. When the light source mode switch has completed the filter change, the light source system controller 90 generates a light source status signal, which is transmitted to the control center 20. Upon receipt of the light source status signal, the control signal routes the video signal from the RGB video camera control unit 48 to the RGB video monitor 54 and the resulting white light image is displayed.

In the case of switching from white light imaging mode into the fluorescence imaging mode, the control center 20 reacts to the first switch signal from the combination camera head 42 by sending a signal to the light source system controller 90 instructing it to move the blue light filter into the light path. A light source status signal is generated and sent the control center 20 when the light source mode switch has completed the filter change. When the control center also receives the second switch signal from the combination camera head 42, indicating that the movable mirror 186 has reached the fluorescence imaging mode position, the control center energizes the ICCDs in the fluorescence camera head 44 and routes the video signals from the fluorescence camera control units to the RGB video monitor 54. The resulting fluorescence image is displayed on the RGB video monitor 54. If the incorrect light source status signal is received by the control center 20, the ICCDs in the fluorescence camera head will not be energized, even if the second switch signal has been received from the combination camera head 42.

Figure 7:
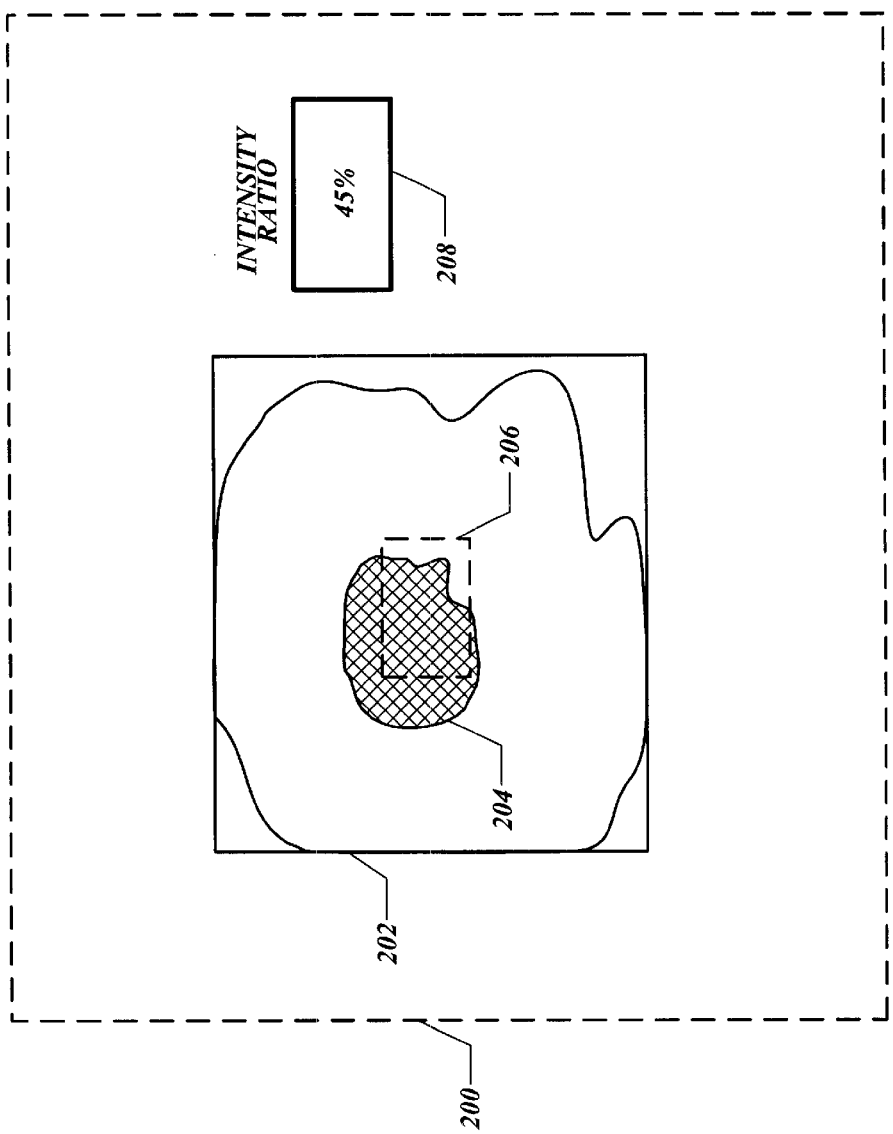
FIG. 7 is a pictorial illustration of an autofluorescence image that includes a quantitative indication of the relative intensities of the autofluorescence light present in two spectral bands in accordance with another aspect of the present invention.

In accordance with another aspect of the present invention, the imaging system of the present invention quantifies the relative brightness of the autofluorescence light produced by the tissue in each of the spectral bands $\Delta\lambda_1$ and $\Delta\lambda_2$ in an objective manner. FIG. 7, shows a monitor display 200 with an image 202 of the tissue under examination. Differences in the autofluorescence spectrum produced by normal and abnormal tissue are shown as areas of different color in the image. For example, abnormal tissue 204 produces proportionally less autofluorescence light in the green portion of the spectrum than normal tissue and is shown as a reddish area in the displayed image.

The relative brightness of the autofluorescence light in the green and red wavebands imaged by the system, $\Delta\lambda_1$ and $\Delta\lambda_2$, can be used as a measure of the difference in the actual fluorescence emission spectra of normal and abnormal tissue. A ratio (or other function relating the $\Delta\lambda_1$ to the $\Delta\lambda_2$ waveband) of the brightness of the tissue autofluorescence in the green and red spectral bands is calculated and displayed to the physician. The ratio is calculated for a small area such as a region 206 defined in the center of the field of view. Since the color ratio can be recalculated on a frame by frame basis in real time, the color ratio displayed represents the average color ratio of the tissue imaged within the bounds of area 206. Although the area 206 is shown as a particular area located in the center of the field of view, other locations within the field of view and larger or smaller areas could be used.

The ratio calculation is implemented as follows: As described above, the video signals from the fluorescence camera control units are routed to the imaging board 28. The imaging board 28 digitizes the video signals such that the video signal amplitudes correspond proportionally to digital grey level values. The central processing unit 22 within the control center 20 reads the data digitized by the imaging board 28 and sums the grey level values of all the red channel digital data within area 206 and divides that sum by the sum of all the green channel data within area 206. The quotient of these two sums is shown as a dimensionless number 208 on the monitor.

As an alternative to displaying a dimensionless number, other non-visual cues could be used to quantify the relative brightness of the tissue autofluorescence in spectral wavebands $\Delta\lambda_1$ and $\Delta\lambda_2$. For example, a tone having a frequency that is dependent upon the ratio of the brightness of the autofluorescence in each spectral band could be produced. Similarly, the frequency of a blinking light could be made to change in proportion to the changing ratio.

While the preferred embodiment of the invention has been illustrated and described in the preceding description, it will be appreciated that various changes can be made therein without departing from the spirit and scope of the invention. The scope of the invention is therefore to be determined from the following claims and equivalents thereto.

APPENDIX A

```
      REM BASE ADDRESS OF BOARD HARDWIRED TO D0000
      DEF SEG = 53248
      REM READ OUT "AGC" LOGO
      GOSUB READLOGO
      REM INITIALIZE DAC'S TO ZERO, SET-UP GAIN AND RANGE
      GOSUB CLEARDAC
      REM MAKESURE ICCD POWER IS OFF
      GOSUB HVPSOFF
      REM STICK IN SOME STARTING VALUES FOR THE GAIN CONTROL
      k0! = .72134/3: REM PORTION OF GAIN FACTOR OF [-?~?] {0.5 V/ln(2)}
      skew! = 1: REM WEIGHTING SHIFT IF deln's ON OPPOSITE SIDES OF '1'
         REM skew <1 SHIFTS EMPHASIS TO LARGER ERROR TERM
      tlo! = 60: REM LOW THRESHOLD IN PERCENTAGE OF FULLSCALE
      thi! = 80: REM HIGH THRESHOLD IN PERCENTAGE OF FULLSCALE
      flo! = 50: REM NOMINAL PERCENTAGE OF IMAGE ABOVE THRESHOLD ON
CHANNEL 5
      fhi! = 50: REM NOMINAL PERCENTAGE OF IMAGE ABOVE THRESHOLD ON
CHANNEL 6
      wlo! = 1!: REM FULL AUTO GAIN WEIGHTING FOR CHANNELS (2 & 5)
      whi! = 1!: REM FULL AUTO GAIN WEIGHTING FOR CHANNELS (3 & 6)
      dband! = .02: REM GAIN DEADBAND IN VOLTS
      rg0! = .014348: rg1! = 1.0494: rg2! = -.00048863#: REM L2PP6 +10% NUMS
      steps = 0: REM RED INCREMENTS AROUND NOMINAL
      REM CHECK TO SEE IF A PREVIOUS CALIBRATION FILE IS DESIRED
300   PRINT "USE PREVIOUS CALIBRATION FILE ('df for default)?*y/n/q)"
      INPUT bob$: IF (bob$ = "q") THEN 10000
      IF (bob$ = "n") THEN 680
      IF (bob$ = "df") THEN
         name$ = "default.age"
         GOTO 500
      END IF
      IF (bob$ <> "y") THAN 300
      PRINT "ENTER THE FILENAME TO READ THE DATA FROM"
      INPUT name$
500   OPEN name$ FOR INPUT AS #1
      INPUT #1, npcn2max!, npcn2min!, blklvl2%, whtlvl2%, size2!
      INPUT #1, npcn3max!, npcn3min!, blklvl3%, whtlvl3%, size3!
      INPUT #1, npcn5max!, npcn5min!, blklvl5%, whtlvl5%, size5!
      IF (npcn3! > npcn3max!) THEN npcn3max! = npcn3!
      IF (npcn5! > npcn5max!) THEN npcn5max! = npcn5!
      IF (npcn6! > npcn6max!) THEN npcn6max! = npcn6!
      IF (npcn2! > npcn2min!) THEN npcn2min! = npcn2!
      IF (npcn3! > npcn3min!) THEN npcn3min! = npcn3!
      IF (npcn5! > npcn5min!) THEN npcn5min! = npcn5!
      IF (npcn6! > npcn6min!) THEN npcn6min! = npcn6!
      REM GO AROUND AGAIN
1400  NEXT i
1450  NEXT j
      REM DETERMINE BLACK LEVEL REFERENCE VALUES BY SLOWLY
INCREASING
      REM REFERENCES UNTIL COUNTS IN EACH CHANNEL FOR DARK IMAGE
ARE
      REM ONE HALF OF FULL COUNTS POSSIBLE ON CHANNEL
      REM SET UP FLAGS TO TRIGGER BLACK LEVEL REF VALUE SAVE
1600  flag2 = 0: flag3 = 0: flag5 = 0: flag6 = 0
      REM SELECT NEW REFERENCE VOLTAGE
2110  lim% = 260
2120  FOR k% [-?=?] 130 TO lim%
      REM SKIP AHEAD IF ALL THE BLACK LEVELS HAVE BEEN DETERMINED
2130  fsum = flag2 + flag3 + flag5 + flag6
2140  IF (fsum > 3) THEN k% = lim%
2150  MSB% = k%\16: REM DETERMINE HIGH BYTE
      lsb% = (k% - (MSB% * 16)) * 16: REM DETERMINE HIGH NIBBLE OF LOW BYTE
      REM NOW START INCREASING REFERENCE LEVELS ON EACH COUNTER
      REM UNTIL COUNTS START TO FALL OFF SIGNIFICANTLY
2230  POKE &H31, MSB%: POKE &H30, lsb%: REM REF4 ==> CH6
      POKE &H33, MSB%: POKE &H32, lsb%: REM REF3 ==> CH5
      POKE &H35, MSB%: POKE &H34, lsb%: REM REF2 ==> CH3
      POKE &H37, MSB%: POKE &H36, lsb%: REM REF1 ==> CH2
      POKE &H38, 0: REM UPDATE DAC'S
2400  GOSUB CLEARCNT
2420  fields1! PEEK(&H0): REM WAIT FOR REQUIRED # OF FIELDS
      IF (fields1! <= 3) THEN 2420
2480  GOSUB READCNTS
      fields2! = PEEK(&H0)
      REM CORRECT FIELDS TO AVERAGE IF IT INCREMENTED DURING
CHANNEL READS
      INPUT #1, npcn6max!, npcn6min!, blklvl6%, whtlvl6%, size6!
      CLOSE #1: GOTO 7500: REM CLOSE INPUT AND SKIP OVER CAL FUNCTIONS
```

APPENDIX A-continued

```
REM INITIALIZE PIXEL COUNTER MAX/MIN'S
680    npcn2max! = 0: npcn3max! = 0: npcn5max! = 0: npcn6max! = 0:
       z! = 200000: npcn2min! = z!: npcn3min! = z!: npcn5min! = z!
       npcn6min! = z!
REM LOOP THROUGH COUNTER READ CYCLES AND PICK OUT MAXIMUM
REM AND MINIMUM COUNTER VALUES . . . SHOULD CONTAIN MAXIMUM COUNTS
REM IF REFERENCE THRESHOLDS ARE SET BELOW BLACK LEVELS
710    FOR j = 0 TO 3: REM GO THROUGH COUNTER SCANNING A FEW TIMES
720    FOR i = 0 TO 15: REM VARY # OF FIELDS TO AVOID LATENCY INDUCED
ALIASING
730    GOSUM CLEARCNT
       REM LET COUNTERS FREE RUN FOR (93 - i) FIELDS
740    fields1! = PEEK(&H0)
       IF (fields1! <= (92 - i)) THEN 740
       REM READ OUT ALL COUNTERS
810    GOSUB READCNTS
       fields2! = PEEK(&H0)
       REM CORRECT FIELDS TO AVERAGE IF FIELDS INCREMENTED DURING
READS
       fields! = (fields1! + fields2!)/2
       REM CALCULATE TOTAL COUNTS IN EACH CHANNEL
       GOSUB MAKECNTS
       REM NORMALIZE COUNTER CONTENTS TO NUMBER OF FIELDS TO
       REM DETERMINE FULL IMAGE COUNT VALUES
1000   npcn2! = ch2!/fields!: npcn3! = ch3!/fields!
       npcn5! = ch5!/fields!: npcn6! = ch6!/fields!
       REM CHECK FOR UNREALISTIC FULL FILL IMAGE COUNT VALUES
1100   flag% = 0: npcn! = 173000: REM npcn! SHOULD BY NOMINAL COUNT VALUE
1120   IF (ABS(1 - (npcn2!/npcn!)) .05) THEN flag% = 1
1130   IF (ABS(1 - (npcn3!/npcn!)) .05) THEN flag% = 1
1150   IF (ABS(1 - (npcn5!/npcn!)) .05) THEN flag% = 1
1160   IF (ABS(1 - (npcn6!/npcn!)) .05) THEN flag% = 1
1170   IF (flag% > 0) THEN 730: REM GO BACK AND START OVER
       REM CHECK FOR HIGHER THAN OR LOWER THAN PREVIOUS EXTREMES
1210   IF (npcn2!>npcn2max!) THEN npcn2max! = npcn2!
       fields! (fields1! + fields2!)/2
       GOSUB MAKECNTS
       REM NORMALIZE COUNTER CONTENTS TO NUMBER OF FIELDS
2900   npcn2! = ch2!/fields!: npcn3! = ch3!/fields!
       npcn5! = ch5!/fields!: npcn6! = ch6!/fields!
       REM CHECK TO SEE IF NEW REFERENCE THRESHOLDS HAVE ELIMINATED
       REM 50% OF POSSIBLE COUNTS ON EACH CHANNEL. IF YES, SET FLAG
       REM AND ASSIGN CURRENT SETTING AS THIS CHANNELS BLACK LEVEL
3030   IF ((flag2 = 0) AND (npcn2! < (.5* npcn2max!)) THEN
          flag2 = 1
          blklvl2% = k%
       END IF
3060   IF ((flag3 = 0) AND (npcn3! < (.5* npcn3max!)) THEN
          flag3 = 1
          blklvl3% = k%
       END IF
4020   IF ((flag5 = 0) AND (npcn5! < (.5* npcn5max!)) THEN
          flag5 = 1
          blklvl5% = k%
       END IF
4050   IF ((flag6 = 0) AND (npcn6! < (.5* npcn6max!)) THEN
          flag6 = 1
          blklvl5% = k%
       END IF
4080   NEXT k%
       REM DETERMINE FULLSCALE (WHITE) REFERENCE LEVEL BY RAISING
GAINS
       REM UNDER USER CONTROL UNTIL SATURATION APPEARS IN EACH
COLOR IN
       REM THE IMAGE THEN LOCK INTENSIFIER GAINS AND RAISE CHANNEL
       REM REFERENCE VOLTAGES UNTIL MAJORITY OF COURTS HAVE BEEN
ELIMINATED.
       REM CORRESPONDING REFERENCE VOLTAGE IS THEN DEFINED AS "FULL
SCALE".
4500   GOSUB HVPSON
       PRINT "PREPARING TO INCREASE INTENSIFIER GAINS"
       PRINT "PLEASE ESTABLISH THE DESIRED ILLUMINATION"
       PRINT
"++++++++++++++++++++WARNING++++++++++++++++++"
       PRINT "+DO NOT ADJUST THE ILLUMINATION DURING WHITE LEVEL
SCANNING+"
       PRINT
"++++++++++++++++++++++++++++++++++++++++++++++"
```

APPENDIX A-continued

```
4520  PRINT "TYPE 'r' WHEN READY, OR 'q' TO QUIT"
      INPUT com$: IF (com$ = "q") THEN 1000: IF (com$ <> "r") THEN 4520
      REM DETERMINE THE REQUIRED INTENSIFIER SETTING TO
      REM PROVIDE SOME SATURATION FOR EACH COLOR CHANNEL
4600  PRINT "TYPE 'u' TO RAISE OR 'd' TO DECREASE THE RED GAIN"
      PRINT "TYPE ANY OTHER KEY TO GO ON TO GREEN CHANNEL"
4620  msb1% = 100: REM STARTING RED VALUE
4630  INPUT dir$
4640  IF ((dir$ <> "u") AND (dir$ <> "d")) THEN
        sat1% = msb1%: REM SAVE CURRENT RED GAIN AS SATURATION GAIN
        POKE&[H53?], 0: POKE&H58, 0: REM RESET RED GAIN TO ZERO
        GOTO 4800: REM JUMP TO GREEN CHANNEL GAIN SET UP
      END IF
4650  IF ((dir$ = "u") AND (msb1% <200)) THENmsb1% = msb1% + 4
      IF ((dir$ = "d") AND (msb1% >0)) THENmsb1% = msb1% – 4
      POKE&H53, msb1%: POKE&H58, 0: GOTO 4630
4800  PRINT "TYPE 'u' TO RAISE OR 'd' TO DECREASE THE GREEN GAIN"
      PRINT "TYPE ANY OTHER KEY TO GO ON"
4820  msb2% = 100: REM STARTING RED VALUE
4830  INPUT dir$
4840  IF ((dir$ <> "u") AND (dir$ <> "d")) THEN
        sat2% = msb2%: REM SAVE CURRENT RED GAIN AS SATURATION GAIN
        POKE&H51, 0: POKE&H58, 0: REM RESET RED GAIN TO ZERO
        GOTO 5000
      END IF
4650  IF ((dir$ = "u") AND (msb2% <200)) THEN msb2% = msb2% + 4
      IF ((dir$ = "d") AND (msb2% >0)) THEN msb2% = msb2% 4
      POKE&H51, msb2%: POKE&H58, 0: GOTO 4830
5000  PRINT "WERE BOTH GAINS SET PROPERLY? (y/n/q)"
      INPUT bob$: IF (bob$ = "q") THEN 10000
      IF (bob$ = "n") THEN 4500
      IF (bob$ <> "y") THEN 5000
      REM IF ALL WAS WELL, RESET SATURATION GAIN VOLTAGES
      REM ON RED AND GREEN AND CONTINUE
5060  POKE &H53, sat1%: POKE &H51, sat2%: POKE &H58, 0
      REM PAUSE TO LET ICCD [IIVPS? HVPS?] SETTLE
5070  FOR i = 1 TO 20000: NEXT i
      REM DETERMINE WHITE LEVEL BY INCREASING THRESHOLDS
      REM UNTIL ALMOST ALL COUNTS ARE ELIMINATED
      REM SET UP FLAGS TO TRIGGER WHITE LEVEL REF VALUE SAVE
5090  flag2 = 0: flag3 = 0: flag5 = 0: flag6 = 0
      max% = 2000
      REM SELECT NEW REFERENCE VOLTAGE
5110  FOR k% = 1500 TO max%
      REM SKIP AHEAD IF ALL THE WHITE LEVELS HAVE BEEN DETERMINED
5120  fsum = flag2 + flag3 + flag5 + flag6
5130  IF (fsum > 5) THEN k% = max%
      MSB% = k%\16: REM HIGH BYTE
      lsb% = (k% – (MSB% * 16)) * 16: REM LOW BYTE
      POKE &H31, MSB%: POKE &H30, lsb%: REM REF4 ==> CH6
      POKE &H33, MSB%: POKE &H32, lsb%: REM REF3 ==> CH5
      POKE &H35, MSB%: POKE &H34, lsb%: REM REF2 ==> CH3
      POKE &H37, MSB%: POKE &H36, lsb%: REM REF1 ==> CH2
      POKE &H38, 0: REM UPDATE DAC'S
5400  GOSUB CLEARCNT
5420  fields1! = PEEK(&H0): REM WAIT FOR REQUIRED # OF FIELDS
      IF (fields1! <= 9) THEN 5420
5480  GOSUB READCNTS
      fields2! = PEEK(&H0)
      REM CORRECT FIELDS TO AVERAGE IF IT INCREMENTED DURING
CHANNEL READS
      fields! = (fields1! + fields2!)/2
      GOSUB MAKECNTS
      REM NORMALIZE COUNTER CONTENTS TO NUMBER OF FIELDS
      pcn2! = ch2!/fields!: pcn3! = ch3!/fields!
      pcn5! = ch5!/fields!: pcn6! = ch6!/fields!
      REM CHECK TO SEE IF NEW REFERENCE THRESHOLDS HAVE ELIMINATED
      REM 99% OF POSSIBLE COUNTS ON EACH CHANNEL. IF YES, SET FLAG
      REM AND ASSIGN CURRENT SETTING AS THIS CHANNELS BLACK LEVEL
6020  IF ((flag2 = 0) AND (pcn2! < (.015 * npcn2max!))) THEN
        flag2 = 1
        whtlvl2% = k%
      END IF
6040  IF ((flag3 = 0) AND (pcn3! < (.015 * npcn3max!))) THEN
        flag3 = 1
        whtlvl3% = k%
      END IF
```

APPENDIX A-continued

```
6080  IF ((flag5 = 0) AND (pcn5! < (.015 * npcn5max!))) THEN
        flag5 = 1
        whtlvl5% = k%
      END IF
6100  IF ((flag6 = 0) AND (pcn6! < (.015 * npcn6max!))) THEN
        flag6 = 1
        whtlvl6% = k%
      END IF
6130  NEXT k%
      REM DETERMINE THE IMAGE SIZE AS A FRACTION OF THE AVAILABLE IMAGE
      REM AREA BY ADJUSTING THE REFERENCE VOLTAGES TO "JUST" ABOVE BLACK
      REM AND COUNTING ALL THE PIXELS THAT EXCEED THIS THRESHOLD
      REM 'up!' IS THE FRACTIONAL INCREASE (IN TERMS OF THE SIGNAL
      REM INPUT RANGE) IN THE THRESHOLD ABOVE THE PREVIOUSLY
      REM DETERMINED BLACK LEVEL (IN MSB)
6200  up! = .05: REM CALCULATE THRESHOLDS CORRESPONDING TO 5% FULLSCALE
        lvl2% = blklvl2% + ((whtlvl2% - blklvl2%) * up!)
        lvl3% = blklvl3% + ((whtlvl3% - blklvl3%) * up!)
        lvl5% = blklvl5% + ((whtlvl5% - blklvl5%) * up!)
        lvl6% = blklvl6% + ((whtlvl6% - blklvl6%) * up!)
        REM LOAD THRESHOLDS
        POKE &H37, (lvl2%\16): REM CH2 MSB
        POKE &H36, (lvl2% - ((lvl2%\16) * 16)) * 16): REM CH2 LSB
        POKE &H35, (lvl3%\16): REM CH3 MSB
        POKE &H34, (lvl3% - ((lvl2%\16) * 16)) * 16): REM CH3 LSB
        POKE &H33, (lvl5%\16): REM CH5 MSB
        POKE &H32, (lvl5% - ((lvl2%\16) * 16)) * 16): REM CH5 LSB
        POKE &H31, (lvl6%\16): REM CH6 MSB
        POKE &H30, (lvl6% - ((lvl2%\16) * 16)) * 16): REM CH6 LSB
        POKE &H38, 0: REM UPDATE DAC'S
6700  oops% = 0: num% = 4
6710  FOR j% = 0 TO num%
6730  GOSUB CLEARCNT
6740  fields1! = PEEK(&H0): REM WAIT FOR REQUIRED # OF FIELDS
        IF (fields1! <= 91) THEN 6740
6780  GOSUBREADCNTS
        fields2! = PEEK*&H0)
        REM CORRECT FIELDS TO AVERAGE IF IT INCREMENTED DURING CHANNEL READS
        fields! = (fields1! + fields2!)/2
        GOSUB MAKECNTS
        REM NORMALIZE COUNTER CONTENTS TO NUMBER OF FIELDS
        pcnsize2! = ch2!/fields!:pcnsize3! = ch3!/fields!
        pcnsize5! = ch5!/fields!:pcnsize6! = ch6!/fields!
        REM CALCULATE AND CHECK FRACTIONAL SIZE OF IMAGE ON EACH CHANNEL
7270  size2! = pcnsize2!/npcn2max!
        IF (size2! > 1.1 OR size2! < .2) THEN oops% = 1
7290  size3! = pcnsize3!/npcn3max!
        IF (size3! > 1.1 OR size3! < .2) THEN oops% = 1
7330  size5! = pcnsize5!/npcn5max!
        IF (size5! > 1.1 OR size5! < .2) THEN oops% = 1
7350  size6! = pcnsize6!/npcn6max!
        IF (size6! > 1.1 OR size6! < .2) THEN oops% = 1
7370  IF (oops% = 0) THEN j% = num%
7380  NEXT j%
7400  IF (oops% <> 0) THEN
        PRINT "INVALID IMAGE SIZES FOUND"
        GOTO 10000
      END IF
      REM SHUT DOWN INTENSIFIER GAIN AND POWER
7430  GOSUB GAINZERO
      GOSUB HVPSOFF
      REM PRINT OUT RESULTS
7500  PRINT "CHANNEL MAXCNT MINCNT BLKLVL WHTLVL SIZE%"
        PRINT "2 "; npcn2max!;" "; npcn2min!;" "; blklvl2%;" "; whtlvl2%;" "; size2!
        PRINT "3 "; npcn3max!;" "; npcn3min!;" "; blklvl3%;" "; whtlvl3%;" "; size3!
        PRINT "5 "; npcn5max!;" "; npcn5min!;" "; blklvl5%;" "; whtlvl5%;" "; size5!
        PRINT "6 "; npcn6max!;" "; npcn6min!;" "; blklvl6%;" "; whtlvl6%;" "; size6!
        REM WRITE CURRENT SETTINGS TO FILE
7570  PRINT "DO YOU WANT TO SAVE THESE TO A FILE? (y/n/q)"
7580  INPUT bob$: IF (bob$ = "q") THEN 10000
        IF (bob$ = "n") THEN 7640
        IF (bob$ <> "y") THEN 7570
7610  PRINT "ENTER THE FILENAME TO SAVE THE DATA UNDER"
7620  INPUT name$
```

APPENDIX A-continued

```
7630  OPEN name$ FOR OUTPUT AS #1
      PRINT #1, npcn2max!, npcn2min!, blklvl2%, whtlvl2%, size2!
      PRINT #1, npcn3max!, npcn3min!, blklvl3%, whtlvl3%, size3!
      PRINT #1, npcn5max!, npcn5min!, blklvl5%, whtlvl5%, size5!
      PRINT #1, npcn6max!, npcn6min!, blklvl6%, whtlvl6%, size6!
   CLOSE #1
      REM REBUILD 'pcnsize' VARIABLES
7640  pcnsize2! = size2! * npcn2max!: pcnsize3! = size3! * npcn3max!
      pcnsize5! = size5! * npcn5max!: pcnsize6! = size6! * npcn6max!
      REM++++++++++++++++++++++++++++++++++++++++++++++++
      REM
      REM         AGC FEEDBACK DETERMINATION
      REM
      REM++++++++++++++++++++++++++++++++++++++++++++++++
7680  PRINT "PREPARING TO ENTER IMAGING MODE"
      PRINT "PLEASE ESTABLISH THE DESIRED ILLUMINATION"
      PRINT "TYPE 'r' WHEN READY, OR 'q' TO QUIT"
      INPUT com$: IF (com$ = "q") THEN 10000: IF (com$ <> "r") THEN 7680
7700  PRINT "SELECT GAIN CONTROL METHOD"
      PRINT "m -> MANUAL, f -> full (MIXED PEAK/AVERAGE)"
      INPUT agcmode$
      IF (agcmode$ = "m") THEN
         PRINT "USE UP/DOWN ARROW KEYS TO CONTROL FINE GAIN"
         PRINT "USE PGUP/PGDOWM[N/?] KEYS TO CONTROL COARSE GAIN"
         GOTO 7900
      END IF
      IF (agcmode$ = "f") THEN GOTO 7900
      GOTO 7700
      REM SET UP DEFAULT THRESHOLDS
7900  temp% = CINT((whtlvl2% - blblvl2%)/16 * (tlo!/100))
      POKE &H37, temp%
      REM SET REF3 AT ABOUT thi% FS IN MSB
      temp% = CINT((whtlvl3% - blblvl3%)/16 * (tli!/100))
      POKE &H35, temp%
      REM SET REF5 AT ABOUT tlo% FS IN MSB
      temp% = CINT((whtlvl5% - blblvl5%)/16 * (tlo!/100))
      POKE &H33, temp%
      REM SET REF6 AT ABOUT thi% FS IN MSB
      temp% = CINT((whtlvl6% - blblvl6%)/16 * (thi!/100))
      POKE &H31, temp%
      POKE &H38, 0: REM UPDATE DAC'S
      GOSUB HVPSON
      PRINT "ENABLING ICCD HVPS"
      now = TIMER
      DO WHILE (now = TIMER)
      LOOP
      REM START CHECKING COUNTERS
      delt0! = 1: delt1! = 1: delt2! = 1
      CLS
      REM SET UP FAULT VARIABLE
      warn% = 0: REM CHECKED FOR >15 FAULTS OUT AND DISABLES ICCD'S
8000  DO WHILE (1 <> 0)
      key$ = INKEY$
      IF ((key$ = "q") or (key$ = "Q")) THEN 9200
      IF ((key$ <> CHR$(0)) AND (agemode$ <> "m")) THEN GOSUB MODVALS: REM
TWEAK RUNNING PARAMETERS
      REM DELAY AND THEN READ REQUIRED NUMBER OF FIELDS
8070  (fields1! = PEEK(&H0)
      IF (fields1! <= 3) THEN 8070
      GOSUB CLEARCNT
8080  FIELDS1! = peek(&[H0?])
      if (fields1! <= 0) THEN 8080
8180  GOSUB READCNTS
      fields2! = PEEK(&H0)
      REM CORRECT FIELDS TO AVERAGE IF IT INCREMENTED DURING
CHANNEL READS
      fields! = (fields1! + fields2!)/2
      GOSUB MAKECNTS
      REM NORMALIZE COUNTS TO NUMBER OF FIELDS AND FULL IMAGE
COUNTS
      REM I.E. 'sx!' IS (AREA ABOVE THRESHOLD/MAXIMUM IMAGE SIZE)
      s2! = ch2!/fields!/pcnsize2!: s3! = ch3!/fields!/pcnsize3!
      s5! = ch5!/fields!/pcnsize5!: s6! = ch6!/fields!/pcnsize6!
      REM++++++++++SIMPLE PSEUDO-PROPORTIONAL AGC WITH
DEADBAND+++++++++++++++++++
      REM+++ERROR TERM BASED UPON WEIGHTED AVERAGE OF INDIVIDUAL
ERRORS+++++
      REM+++++++++++++++++FOUR SAMPLE LEAKY INTEGRAL
```

APPENDIX A-continued

```
ACTION+++++++++++++++++++++
      REM CAN'T HAVE MORE THAN ALL THE IMAGE
8700  IF (s2! > 1) THEN s2! = 1: IF (s3! > 1) THEN s3! = 1
      IF (s5! > 1) THEN s5! = 1: IF (s6! > 1) THEN s6! = 1
      REM RELATIVE AMOUNT OF IMAGE IN RELATION TO DESIRED LEVEL
      del2! = (s2!/(flo!/100))
      del3! = (s3!/(thi!/100))
      del5! = (s5!/(flo!/100))
      del6! = (s6!/(thi!/100))
      REM SKIP PAST AUTOMATIC GAIN CHANGE DETERMINATION IF IN
MANUAL MODE
      IF (agcmode$ = "m") THEN
         GOSUB MANUALdg
         GOTO 8850
END IF
REM CHECK FOR SEVERE OVERSATURATION CONDITIONS
IF ((del2! > 6) OR (del6! > 6)) THEN
         warn% = warn% - 1: REM CHARGE WARNING VALUE
      ELSE
         warn% = warn% + 1: REM DISCHARGE WARNING VALUE
         IF (warn% < 0) THEN warn% = 0
      END IF
      REM IF SATURATED TO[TOO/?] MANY TIMES IN A ROW, CRASH AND BURN
      IF (warn% > 25)THEN
         GOSUB HVPSOFF
         FOR i = 58 TO 74 STEP 4
         SOUND (EXP(i/10)), 1
         NEXT i
         PRINT "AGC UNABLE TO PREVENT SERIOUS SATURATION"
         PRINT "PLEASE VERIFY SYSTEM SETTINGS AND CONFIGURATION"
         GOTO 9200
      END IF
      IF (warn% > 16) THEN SOUND 3600, 1
      REM ARBITRATE GAIN CONTROL INPUTS BASED UPON
      REM RELATIVE RED AND GREEN IMAGE FILLS
      IF ((del5! >= del2!) AND (del6! >= del3!)) THEN
      REM GREEN IMAGE CONTAINS HIGHEST RELATIVE IMAGE FILLS
THEREFORE
      REM GENERATE A WEIGHTED ERROR VALUE ONLY FROM GREEN VALUES
      IF (SGN(1 - del5!) = SGN(1 - del6!)) THEN
         delt3! = ((wlo! * del5!) + (whi! * del6!))
         delt3! = delt3!/(wlo! + whi!)
         MODE$ = "5AND6"
      END IF
      IF ((del5! < 1) AND (del6! > 1)) THEN
         REM SLIGHTLY SHIFT WEIGHTING TOWARDS CHANNEL 5
         delt3! = ((skew! * wlo! * del5!) + (whi!/skew! * dcl6!))
         delt3! = delt3!/(skew! * wlo! + whi!/skew!)
         MODE$ + "5OVER6"
      END IF
      IF ((del6! < 1) AND (del5! > 1)) THEN
         REM SLIGHTLY SHIFT WEIGHTING TOWARDS CHANNEL 6
         delt3! = ((wlo!/skew! * del5!) + (skew! * whi! * dcl[del?]6!))
         delt3! = delt3!/(wlo!/skew! + skew! * whi!)
         MODE$ + "6OVER5"
      END IF
      ELSEIF ((del2! >= del5!) AND (del3! >= del6!)) THEN
         REM RED IMAGE CONTAINS HIGHEST RELATIVE IMAGE FILLS
THEREFORE
      REM GENERATE A WEIGHTED ERROR VALUE ONLY FROM RED VALUES
      IF (SGN(1 - del2!) = SGN(1 - del3!)) THEN
         delt3! = ((wlo! * del2!) + (whi! * del3!))
         delt3! = delt3!/(wlo! + whi!)
         MODE$ = "2AND3"
      END IF
      IF ((del2! < 1) AND (del3! > 1)) THEN
         REM SLIGHTLY SHIFT WEIGHTING TOWARDS CHANNEL 2
         delt3! = ((skew! * wlo! * del2!) + (whi!/skew! * del3!))
         delt3! = delt3!/(skew! * wlo! + whi!/skew!)
         MODE$ = "2OVER3"
      END IF
      IF ((del3! < 1) AND (del2! > 1)) THEN
         REM SLIGHTLY SHIFT WEIGHTING TOWARDS CHANNEL 3
         delt3! = ((wlo!/skew! * del2!) + (skew! * whi! * del3!))
         delt3! = delt3!/(wlo!/skew! + skew! * whi!)
         MODE$ + "3OVER2"
      END IF
      REM IF NEITHER RED OR GREEN IS CLEARLY DOMINANT, MIX RESULTS
      REM TO GENERAL AN ERROR TERM
```

APPENDIX A-continued

```
        ELSEIF ((del5! >= del2!) AND (del3! >= del6!)) THEN
          REM GREEN MID AND RED PEAK
          IF (SGN(1 - del5!) = SGN(1 - del3!)) THEN
            delt3! = ((wlo! * del5!) + (whi! * del3!))
            delt3! = delt3!/(wlo! + whi!)
            MODE$ = "5AND3"
          END IF
          IF ((del5! < 1) AND (del3! > 1)) THEN
            REM SLIGHTLY SHIFT WEIGHTING TOWARDS CHANNEL 5
            delt3! = (skew! * wlo! * del5!) + (whi!/skew! * del3!))
            delt3! = delt3!/(skew! * wlo! + whi!/skew!)
            MODE$ = "5OVER3"
          END IF
          IF ((del3! <= 1) AND (del5! > 1)) THEN
            REM SLIGHTLY SHIFT WEIGHTING TOWARDS CHANNEL 3
            delt3! = ((wlo!/skew! * del5!) + (skew! * whi! * del3!))
            delt3! = delt3!/(wlo! /skew!+ skew! * whi!)
            MODE$ = "3OVER5"
          END IF
        ELSEIF ((del2! >= del5!) AND (del6! >= del3!)) THEN
          REM RED MID AND GREEN PEAK
          IF (SGN(1 - del2!) = SGN(1 - del6!)) THEN
            delt3! ((wlo! * del2!) + (whi! * del6!))
            delt3! = delt3!/(wlo! whi!)
            MODE$ = "2AND6"
          END IF
          IF ((del2! < 1) AND (del6! > 1)) THEN
            REM SLIGHTLY SHIFT WEIGHTING TOWARDS CHANNEL 2
            delt3! = ((skew! * wlo! * del2!) + (whi!/skew! * del6!)
            delt3! = delt3!/(skew! * wlo! + whi!/skew!)
            MODE$ = "2OVER6"
          END IF
          IF ((del6! < 1) AND (del2! > 1)) THEN
            REM SLIGHTLY SHIFT WEIGHTING TOWARDS CHANNEL 6
            delt3! = ((who!/skew! * del2!) + (skew! * whi! * del6!))
            delt3! = delt3!/(wlo!/skew! + skew! * whi!)
            MODE$ = "6OVER2"
          END IF
ELSE
          REM IF SITUATION GETS TO HERE, MUST HAVE MISSING TEST CASE
          REM RUN IN SMALL CIRCLES AND PANIC
          BEEP
          LOCATE 20, 18
          PRINT "del2="; del2!, "del3="; delt3!," del5="; del5!, "del6="; del6!
          GOTO10000
        END IF
        REM FOUR SAMPLE INTEGRATOR WITH GEOMETRIC DECAY '1/{(t-t0)^ 2}'
        REM++++++++++++++++++++++++++++++++++++++++++++++++++++++++
        REM BUILD delt! FROM RECENT GAIN CHANGE HISTORY OF dcltn!'s
8720    delt! = (delt3! + delt2!/3 + delt1!/9 + delt0!/27)
        delt! - delt!/(1 + 1/3 + 1/9 + 1/27): REM PRESERVE SCALE
        REM SHIFT deltn!'s ONE PERIOD OLDER
        delt0! = delt1!: delt1! = delt2!: delt2! = delt3!
        REM PROTECT 'LOG' FROM NEAR ZERO OR LARGE 'delt!' VALUES
        IF (delt! < .000001) THEN delt! = .000001: REM LIMITS MAXIMUM DOWN STEP
        IF (delt! > 1000000) THEN delt! = 1000000: REM LIMITS MAXIMUM UP STEP
        REM LOG RESPONSE TO COMPLEMENT (e^V) BEHAVIOR[BEHAVIOR /?]
        REM NOTE THAT LARGE delt! CAUSES NEGATIVE dg!
        dg! = -1 * LOG(delt!) * k0!
        IF (dg! > 2) THEN dg! = 2: REM OVERRIDE MAXIMUM UP STEP
        REM NOW APPLY GAIN CHANGE, DEADBAND AND FAILURE LIMITS
8800    IF (ABS(dg!) <= dband!) THEN dg! = 0: REM APPLY DEADBAND
        REM APPLY GAIN CHANGE
        REM --> ASSUMES RED AND GREEN HAVE SIMILAR d/dV {Krel[?]}
CHARACTERISTICS
8850    g! = g! + dg!
        IF (g! < .01) THEN g! = .01: REM BOTTOM GAIN LIMIT
        IF (g! > 9.3) THEN g! = 9.3: REM TOP GAIN LIMIT
        gain% = g! * 4096/10: REM GREEN GAIN SETTING IN PARTS PER 4096
        REM SEND OUT NEW INTENSIFIER GAIN REQUESTS
8900    grnmsb% = gain%\16
        grnlsb% = (gain% - (grnmsb% * 16)) * 16
        r! = rg0! + g! * rg1! + (g! ^ 2) * rg2!: REM RED GAIN IN VOLTS
        rgain% = CINT((r! * 4096)/10): REM RED GAIN SETTING IN PARTS PER 4096
        redmsb% = rgain%\16
        redlsb% = (rgain% - (redmsb% * 16)) * 16
        REM SEND OUT NEW CONTROL VOLTAGES
9000    POKE &H53, redmsb%: POKE &H52, redlsb%
        POKE &H51, grnmsb%: POKE &H50, grnlsb%
```

APPENDIX A-continued

```
       POKE &H58, 0
       locate 16, 27
       format3$ = "&##.##&##.##&&"
       COLOR 14
       PRINT USING format3$; "GRN ="; g!; "RED =";r!;" ";MODE$
       LOCATE 19, 20
       COLOR 4
       format4$ = "&##.##&##.##&##.##&##.##"
       PRINT USING format4$; "del2="; del2!; "del3="; del3!; "del5="; del5!; "del6=": del6!
9100   LOOP
```

The embodiments of the invention in which an exclusive property or privilege is claimed are defined as follows:

1. An imaging system for fluorescence endoscopy, comprising:
   a light source that produces fluorescence excitation light;
   an endoscope that delivers the fluorescence excitation light to tissue under examination in vivo and collects autofluorescence produced by the tissue;
   a dual channel fluorescence camera containing a first and second high sensitivity imaging device that receive the autofluorescence in a first and second spectral band and produce electronic signals that are representative of the tissue under examination;
   a control center, including an image processing board that receives the electronic signals produced by the dual channel fluorescence camera wherein said control center causes an image of the tissue under examination to be processed, stored and displayed on a video monitor;
   an automatic gain control circuit that determines a distribution of intensity levels in the electronic signals produced by the dual channel fluorescence camera and adjusts a gain of the first and second high sensitivity image device and/or adjusts a light source intensity based on said distribution of the intensity levels such that the relative gain between the first and second high sensitivity imaging devices follows substantially a polynomial; and
   a video monitor that receives the video signals produced by the image processing board and displays an image of the tissue under examination.

2. The imaging system for fluorescence endoscopy of claim 1, wherein the automatic gain control circuit comprises:
   a plurality of time-over-threshold counters that determine an image area in one or more video fields that have intensities above a plurality of predetermined thresholds.

3. The imaging system for fluorescence endoscopy of claim 2, wherein the time-over-threshold counters further comprise:
   a clock signal having a frequency substantially equal to a pixel clock of the dual channel fluorescence camera;
   a gating circuit that passes the clock signal during an active portion of the electronic signals produced by the dual channel fluorescence camera;
   a plurality of counters that count pulses of the gated clock signal;
   a plurality of comparators having the electronic signals produced by the dual channel fluorescence camera connected to a first input and a programmable reference voltage connected to another input such that when the magnitude of the electronic signals exceed the reference voltage of the comparator, the comparator produces an output which enables one of the plurality of counters; and
   a processor that is programmed to adjust a gain of the high sensitivity imaging device and/or to adjust the light source intensity such that the distribution of intensity levels in one or more video fields substantially equals a desired distribution.

4. The imaging system for fluorescence endoscopy of claim 1, wherein the light source is programmable to produce fluorescence excitation light or white light, the system further comprising:
   a color video camera coupled to receive light collected by the endoscope;
   a light path directing mechanism selectively positioned to direct light collected by the endoscope to the dual channel fluorescence camera or to the color video camera;
   at least one switch that produces a signal that is indicative of the position of the light path directing mechanism; and
   a light source controller that receives the signal from the switch and causes the light source to produce white light after the signal produced by the switch indicates that the light path directing mechanism is positioned to direct the light collected by the endoscope to the color video camera.

5. The imaging system for fluorescence endoscopy of claim 4, wherein the light source controller causes the light source to stop producing white light and begin producing fluorescence excitation light before the light path directing mechanism is moved from a position where light collected from the endoscope is directed to the color video camera to a position where light collected from the endoscope is directed to the dual channel fluorescence camera.

6. The imaging system for fluorescence endoscopy of claim 1, wherein the first high sensitivity imaging device receives autofluorescence in a first spectral band and the second high sensitivity imaging device receives autofluorescence in a second spectral band, the imaging system further comprising a central processing unit that produces a quantitative indication of the intensity of the autofluorescence light in the first spectral band versus the intensity of autofluorescence light in the second spectral band.

7. An imaging system for white light and fluorescence endoscopy, comprising:
   a light source that produces white light and fluorescence excitation light;
   an endoscope that delivers the light to tissue under examination in vivo and collects reflected light or autofluorescence light produced by the tissue sample;
   a fluorescence camera containing a first and second high sensitivity imaging device that receive the autofluorescence in a first and second spectral band and produce electronic signals that are representative of the tissue under examination;

a color video camera that receives the reflected illumination light collected by the endoscope and produces electronic signals that are representative of the tissue under examination;

a control center, including an image processing board, that receives the electronic signals produced by the dual channel fluorescence camera or the color video camera and said control center causes an image of the tissue under examination to be processed, stored and displayed on a video monitor;

a mode switch mechanism including:
(i) a light director that is selectively positioned to direct light collected by the endoscope to the fluorescence camera or to the color video camera;
(ii) a sensing mechanism that senses the position of the light director; and
(iii) a mechanism that operates to change the light source to produce either fluorescence excitation light or white light according to the sensed position of the light director in order to protect the fluorescence camera from reflected white light; and a video monitor that receives video signals produced by the image processing board and displays an image of the tissue under examination.

8. The imaging system for white light and fluorescence endoscopy of claim 7, further comprising:
an automatic gain control circuit within the control center that determines a distribution of intensity levels in the electronic signals produced by the first and second high sensitivity imaging devices and adjusts a gain of the high sensitivity imaging devices and/or adjusts the light source intensity based on said distribution of intensity levels such that the relative gain between the first and second high sensitivity imaging devices follows substantially a polynomial.

9. The imaging system for white light and fluorescence endoscopy of claim 8, wherein the automatic gain control circuit comprises:
a plurality of time-over-threshold counters that determine an image area in one or more video fields that have intensities above a plurality of predetermined thresholds.

10. The imaging system for white light and fluorescence endoscopy of claim 9, wherein the time-over-threshold counters further comprise:
a clock signal having a frequency substantially equal to a pixel clock of the first and second high sensitivity imaging devices;
a gating circuit that passes the clock signal during an active portion of the electronic signals produced by the dual channel fluorescence camera;
a plurality of counters that count pulses of the gated clock signal;
a plurality of comparators having the electronic signals produced by the dual channel fluorescence camera connected to a first input and a programmable reference voltage connected to another input such that when the magnitude of the electronic signals exceed the reference voltage of the comparator, the comparator produces an output which enables one of the plurality of counters; and
a processor that is programmed to adjust a gain of the high sensitivity imaging devices and/or to adjust the light source intensity such that the distribution of intensity levels in one or more video fields substantially equals a desired distribution.

11. An imaging system for fluorescence endoscopy, comprising:
a light source that produces fluorescence excitation light;
an endoscope that delivers the fluorescence excitation light to tissue under examination in vivo and collects autofluorescence produced by the tissue;
a dual channel fluorescence camera containing a first and second high sensitivity imaging device that receive the autofluorescence in a first and second spectral band and produce electronic signals that are representative of the tissue under examination;
a control center including an image processing board that receives the electronic signals produced by the dual channel fluorescence camera wherein said control center causes an image of the tissue under examination to be displayed on a video monitor;
an automated gain control circuit that determines the distribution of intensity levels in the electronic signals produced by the dual channel fluorescence camera and adjusts the gain of the first and second high sensitivity imaging device and/or adjusts a light source intensity based on the distribution of intensity levels such that the relative gain between the first and second high sensitivity imaging device follows substantially a polynomial, the automatic gain control circuit including:
(a) a plurality of time-over-threshold counters that determine an area in one or more video fields having intensities above a plurality of predetermined thresholds, the time-over-threshold counters including a clock signal having a frequency substantially equal to a pixel clock of a dual channel fluorescence camera;
(b) a gating circuit that passes the clock signal during an active portion of the electronic signals produced by the dual channel fluorescence camera;
(c) a plurality of counters that count pulses of the gated clock signals;
(d) a plurality of comparators having the electronic signals produced by the dual channel fluorescence camera connected to a first input and a programmable reference voltage connected to another input such that when the magnitude of the electronic signals exceed the reference voltage of the comparator, the comparator produces an output that enables one of the plurality of counters; and
(e) a processor that is programmed to adjust the gain of the high sensitivity imaging devices and/or to adjust the light source intensity such that the distribution of intensity levels in one or more video fields substantially equals a desired distribution.

12. An imaging system for white light and fluorescence endoscopy, comprising:
a light source that produces white light and fluorescence excitation light;
an endoscope that delivers the light to the tissue under examination in vivo and collects reflected light or autofluorescence light produced by the tissue sample;
a fluorescence camera containing a first and second high sensitivity imaging device that receive the autofluorescence in a first and second spectral band and produce electronic signals that are representative of the tissue under examination;

a color video camera that receives the reflected illumination light collected by the endoscope and produces electronic signals that are representative of the tissue under examination;

a control center, including an imaging processing board, that receives the electronic signals produced by the dual channel fluorescence camera or the color video camera, and said control center causes an image of the tissue under examination to be processed, stored and displayed on a video monitor;

an automatic gain control circuit within the control center that determines a distribution of intensity levels in the electronic signals produced by the first and second high sensitivity imaging devices and adjusts a gain of the high sensitivity imaging devices and/or adjusts the light source intensity based on the distribution of intensity levels such that the relative gain between the first and second high sensitivity imaging devices follows substantially a polynomial, the automated gain control circuit including:

a plurality of time-over-threshold counters that determine an image area in one or more video fields having intensities above a plurality of predetermined thresholds, the time-over-threshold counters including;

a clock signal having a frequency substantially equal to a pixel clock of the first and second high sensitivity imaging devices;

a gating circuit that passes the clock signal during an active portion of the electronic signals produced by the dual channel fluorescence camera;

a plurality of counters that count pulses of the gated clock signal;

a plurality of comparators having the electronic signals produced by the dual channel fluorescence camera connected to a first input and a programmable reference voltage connected to another input such that when the magnitude of the electronic signals exceeds the reference voltage of the comparator, the comparator produces an output which enables one of the plurality of counters; and a processor that is programmed to adjust the gain of the high sensitivity imaging devices and/or to adjust the light source and intensity such that the distribution and intensity levels in one or more video fields substantially equals a desired distribution;

a mode switch mechanism including:
(i) a light detector that is selectively positioned to direct light collected by the endoscope to the fluorescence camera or to the color video camera; and
(ii) a mechanism that operates to change the light source to produce either fluorescence excitation light or white light according to the position of the light director; and a video monitor that receives the signals produced by the image processing board and displays an image of the tissue under examination.

13. An autofluorescence imaging system, comprising:

a light source that produces excitation light;

an endoscope that delivers the excitation light to tissue under examination in vivo and collects autofluorescence produced by the tissue;

a dual channel fluorescence camera having a first and second imaging device having pixels that produce signals in response to applied light and a beam splitter for dividing the autofluorescence into a first and second spectral band such that the first imaging device receives the autofluorescence in the first spectral band and the second imaging device receives the autofluorescence in the second spectral band;

an automatic gain control circuit that adjusts the gain of the first and second imaging devices based on a distribution of pixel intensity levels within an image area of the signals produced by the first and second imaging devices in response to the first and second spectral bands of autofluorescence such that the gain of the first and second imaging devices follows substantially a polynomial;

an image processing board that receives electronic signals produced by the first and second imaging devices and produces corresponding video signals; and a video monitor that receives the video signals from the imaging processing board and displays an image of the tissue.

14. The autofluorescence imaging system of claim 13, wherein the distribution includes a number of pixels within the image area of each of the first and second imaging devices having intensities that are greater than a desired peak value and a desired average value within the image area.

15. An autofluorescence imaging system, comprising:

a light source that produces white light and excitation light;

an endoscope that directs the excitation light to a tissue sample in vivo and collects autofluorescence produced by the tissue;

a dual channel fluorescence camera, including a first and second imaging device having pixels that produce signals in response to applied light and a beam splitter for splitting the autofluorescence into to a first and second spectral band and simultaneously directing autofluorescence in a first spectral band to the first imaging device and autofluorescence in the second spectral band to the second imaging device;

a color video camera that receives reflected white light collected by the endoscope and produces electronic signals that are representative of the tissue under examination;

a mode switch having:
(i) a light director that is selectively positioned to direct light collected by the endoscope to the dual channel fluorescence camera or to the color video camera;
(ii) one or more detectors for detecting the position of the light director;
(iii) a mechanism that operates to change the light source to produce either fluorescence excitation light or white light, according to the detected position of the light director;

an automatic gain control circuit for adjusting a gain of the first and second imaging device based on an intensity distribution of pixel values within an image area of the signals produced by the first and second imaging devices in response to the autofluorescence light in the first and second spectral bands;

an image processing board that receives signals from each of the first and second imaging devices and produces corresponding video signals; and a video monitor that receives the video signals and displays an image of the tissue sample.

16. An autofluorescence imaging system comprising:

a light source that produces excitation light;

an endoscope that directs the excitation light to a tissue sample in vivo and collects autofluorescence produced by the tissue;

a dual channel camera including a first and second high sensitivity image detector having pixels that produce signals in response to applied autofluorescence and a beam splitter for splitting the autofluorescence into a first and second spectral band and for directing the autofluorescence in the first spectral band to the first image detector, and the autofluorescence in the second spectral band to the second image detector;

an image processing board that receives signals from each of the first and second image detectors and produces corresponding video signals; and means for determining a distribution of pixel-intensity values in an image area of the signals produced by the first and second image detectors and for adjusting the relative gain of the first and second image detectors and/or the intensity of the excitation light based on the distribution determined such that the gain between the first and second image detectors follows substantially a polynomial.

17. The system of claim 16, wherein the gain of the first and second image detectors and/or intensity of the excitation light are adjusted such that the distribution includes a number of pixels within the image area having intensities that are greater than a desired peak value and number of pixels with a desired average value.

18. An autofluorescence imaging system comprising:

a light source that produces excitation light;

an endoscope that directs the excitation light to a tissue sample in vivo and collects autofluorescence produced by the tissue;

an autofluorescence camera, including a first and second image detectors, that produces an image of the tissue; and an automatic gain control circuit that determines a distribution of pixel intensity values in an area of the image produced by the autofluorescence camera and adjusts the gain of the first and second image detectors and/or the intensity of the excitation light based on the determined pixel intensity distribution such that the gain of the first and second image detectors maintains a substantially polynomial.

* * * * *

UNITED STATES PATENT AND TRADEMARK OFFICE
CERTIFICATE OF CORRECTION

PATENT NO. : 6,462,770 B1
DATED : October 8, 2002
INVENTOR(S) : R. W. Cline et al.

It is certified that error appears in the above-identified patent and that said Letters Patent is hereby corrected as shown below:

<u>Title page,</u>
Item [56], References Cited, U.S PATENT DOCUMENTS, insert in appropriate order:
-- 4,532,918    8/1985       Wheeler
   4,821,117    4/1989       Sekiguchi
   5,134,662    7/1992       Bacus et al.
   5,165,079    11/1992      Schulz-Hennig
   5,225,883    7/1993       Carter et al.
   5,255,087    10/1993      Nakamura et al.
   5,420,628    5/1995       Poulsen et al.
   5,430,476    7/1995       Häfele et al.
   6,008,889    12/1999      Zeng et al.
   6,021,344    2/2000       Lui et al.
   6,069,689    5/2000       Zeng et al. --
Reference "4,155,812 A 5/1979" should read -- 4,115,812 9/1978 --; and
"Kancko et al." should read -- Kaneko et al. --

FOREIGN PATENT DOCUMENTS, insert in appropriate order:
-- JP    H07-155286        6/1995
   JP    H07-155290        6/1995
   JP    H07-155291        6/1995
   JP    H07-155292        6/1995
   JP    H7-155285         6/1995
   JP    7-204156-A        8/1995
   JP    H07-250812        10/1995
   JP    H7-250804         10/1995
   JP    8-224208          9/1996
   JP    8-224209          9/1996
   JP    8-224240          9/1996
   DE    196 08 027 A1     9/1996
   JP    10-151104-A       6/1998
   JP    10-201700-A       8/1998
   JP    10-104070-A       4/1999
   JP    11-155812         6/1999 --

UNITED STATES PATENT AND TRADEMARK OFFICE
CERTIFICATE OF CORRECTION

PATENT NO.     : 6,462,770 B1
DATED          : October 8, 2002
INVENTOR(S)    : R. W. Cline et al.

It is certified that error appears in the above-identified patent and that said Letters Patent is hereby corrected as shown below:

Item [57], ABSTRACT,
Line 7, "transducers are" should read -- transducers is --
Line 12, "the-" should read -- the --
Line 13, "used to produced" should read -- used to produce --
Line 23, "pass to fluorescence" should read -- pass to a fluorescence --

Column 27,
Line 67, "exceed" should read -- exceeds --

Column 29,
Line 62, "exceed" should read -- exceeds --

Column 30,
Line 48, "exceed" should read -- exceeds --

Column 32,
Line 37, "into to a" should read -- into a --

Column 34,
Line 14, "image detectors," should read -- image detector, --
Lines 23-24, "maintains a substantially polynomial." should read
-- follows substantially a polynomial. --

Signed and Sealed this

Twenty-third Day of September, 2003

JAMES E. ROGAN
*Director of the United States Patent and Trademark Office*